United States Patent
Kolkman et al.

(10) Patent No.: US 12,421,508 B2
(45) Date of Patent: Sep. 23, 2025

(54) SERINE PROTEASES

(71) Applicant: DANISCO US INC., Palo Alto, CA (US)

(72) Inventors: Marc Kolkman, Oegstgeest (NL); Rie Mejldal, Østbirk (DK); Anja Hemmingsen Kellett-Smith, Århus C (DK); Lilia Maria Babe, Emerlad Hills, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 18/635,214

(22) Filed: Apr. 15, 2024

(65) Prior Publication Data

US 2024/0301384 A1 Sep. 12, 2024

Related U.S. Application Data

(60) Division of application No. 17/336,647, filed on Jun. 2, 2021, now Pat. No. 11,987,825, which is a continuation of application No. 15/884,749, filed on Jan. 31, 2018, now abandoned, which is a continuation of application No. 15/521,386, filed as application No. PCT/US2015/057526 on Oct. 27, 2015, now abandoned.

(60) Provisional application No. 62/069,184, filed on Oct. 27, 2014.

(51) Int. Cl.
| | |
|---|---|
| *C12N 9/64* | (2006.01) |
| *C11D 3/386* | (2006.01) |
| *C12N 9/54* | (2006.01) |
| *C12N 15/70* | (2006.01) |
| *C12N 15/75* | (2006.01) |
| *C12N 15/76* | (2006.01) |
| *C12N 15/77* | (2006.01) |
| *C12N 15/78* | (2006.01) |

(52) U.S. Cl.
CPC ............ *C12N 9/6424* (2013.01); *C11D 3/386* (2013.01); *C12N 9/54* (2013.01); *C12N 15/70* (2013.01); *C12N 15/75* (2013.01); *C12N 15/76* (2013.01); *C12N 15/77* (2013.01); *C12N 15/78* (2013.01); *C12Y 304/21062* (2013.01)

(58) Field of Classification Search
CPC ........ C12N 9/6424; C12N 9/54; C12N 15/70; C12N 15/75; C12N 15/76; C12N 15/77; C12N 15/78; C11D 3/386; C12Y 304/21062
See application file for complete search history.

*Primary Examiner* — Ganapathirama Raghu

(57) ABSTRACT

The present disclosure relates to serine proteases and variants thereof. Compositions containing the serine proteases are suitable for use in cleaning fabrics and hard surfaces, as well as in a variety of industrial applications.

11 Claims, 7 Drawing Sheets

Specification includes a Sequence Listing.

```
                                                 1         10        20        30        40        50        60
                                                 |         |         |         |         |         |         |
                         BspAL03279               AQAIPWGISQISAPEAQIAGFTGEGVNVAVLDTGIE-DHPDLNVQGGVSFVQGEPD-YQD
                         Bpan04382                AQTIPWGISQISAPEAQIAGFTGEGVNVAVLDTGIE-DHPDLNVQGGVSFVQGEPD-YQD
                         BspAK01305               AQSIPWGIERIGTPAAHASGFTGSGVSVAVLDTGID-PHSDLNVQGGVSFVPGESG-ADD
                         Bohn00569                AQSIPWGIERIGTPAAQASGFTGSGVSVAVLDTGID-PHSDLNIQGGVSFVPGESG-SDD
                    B.sp_B001_ADK62564.1          AQSIPWGIERIGTPAAQASGFTGSGVSVAVLDTGID-PHSDLNVQGGVSFVPGESG-ADD
         Geomicrobium_sp_JCM19038_WP_042417589.1  SQTIPWGIDRVNAPAANASGVTGGGVSVAILDTGIS-THEDLNIQGGESFVPGEPG-IDD
         Geomicrobium_sp_JCM_19055_WP_042358689.1 SQTIPWGIDRVNAPAANASGVTGGGVSVAVLDTGIS-THEDLNIQGGESFVPGEPG-IDD
         Geomicrobium_sp_JCM_19037_WP_042398727.1 SQTIPWGIDRVQATAAHNRGITGNGVRVAVLDTGIS-NHPDLNIQGGTSFVPGEPG-IAD
                    Bacillus_okhensis_WP_034632645.1 NQTIPWGITRVQAPAAINRGFTGAGVRVAVLDTGIS-NHPDLNIRGGVSFVPGEST-YQD
                         B_gibsonii_AGS78407.1    QQTVPWGITRVQAPAVHNRGITGSGVRVAILDSGIS-AHSDLNIRGGASFVPGEPT-TAD
                         B_lentus_P29600          AQSVPWGISRVQAPAAHNRGLTGSGVKVAVLDTGIS-THPDLNIRGGASFVPGEPS-TQD
                    WO2015044206-0010             AQSIPWGISRVQAPAAHNRGLTGSGVKVAVLDTGIS-THEDLNIRGGASFVPGEPS-TQD
                         Bps02003                 NQTVPWGIAQVQAPQAHELGHSGSGTKVAVLDTGIA-EHADLFIHGGASFVAGEPD-YHD
                    B_pseudofirmus_ADC49870       AQTVPWGIPYIYSDVVHRQGYFGNGVKVAVLDTGVA-PHPDLHIRGGVSFISTENT-YVD
                    B_licheniformis_CAJ70731.1    AQTIPYGIPLIKADKVQAGGFKGANVKVAVLDTGIQASHPDLNVGGASFVAGEAY-NTD
                    B_sp_sprD_AAC43581            AQTVPYGVPHIKADVAHAQNVTGSGVKVAVLDTGIDASHEDLRVVGGASFVSEEPDALTD
                    Bacillus_sp_BAD11988          AQTTPWGVTHINAHRAHSSGVTGSGVKVAILDTGIHASHPDLNVRGGASFISGESNPYID
                    Bacillus_sp_sprC_AAC43580     AQTVPWGIPHIKADKAHAAGVTGSGVKVAILDTGIDANHADLNVKGGASFVSGEPNALQD
                    B_amyloliquefaciens_CAA24990  AQSVPYGVSQIKAPALHSQGYTGSNVKVAVIDSGIDSSHPDLKVAGGASMVPSETNPFQD
                    B_atrophaeus_YP003972439      AQSVPYGISQIKAPAVHSQGYTGSNVKVAVIDSGIDSSHPDLKVSGGASFVPSEPNPFQD
```

FIG. 2A

| Label | Sequence |
|---|---|
| BspAL03279 | GNGHGTHVAGTIAALDNDEGVIGVAPNADLYAVKVLGANGSGSVSSIAQGLEWAGENGMD |
| Bpan04382 | GNGHGTHVAGTIAALDNDEGVIGVAPNADLYAVKVLGANGSGSVSSIAQGLEWAGENGMD |
| BspAK01305 | GNGHGTHVAGTIAALDNDEGVLGVAPEVDLFAVKVLSASGSGSISSIAQGLEWTAENNID |
| Bohn00569 | GNGHGTHVAGTIAALDNDQGVLGVAPDVDLFAVKVLSASGSGSISSIAQGLEWTAENNID |
| B.sp_B001_ADK62564.1 | GNGHGTHVAGTIAALDNDEGVLGVAPEVDLFAVKVLSASGSGSISSIAQGLEWAAENNID |
| Geomicrobium_sp_JCM19038_WP_0424l7589.1 | GNGHGTHVAGTIAALDNDLGVLGVSPDVDLYAVKVLGSDGSGNISSIAEGLEWAGENGMD |
| Geomicrobium_sp_JCM_19055_WP_042358689.1 | GNGHGTHVAGTIAALDNDTGVVGVSPDADLYAVKVLGSDGSGNISSIAQGLQWAGENGMD |
| Geomicrobium_sp_JCM_19037_WP_042398727.1 | GNGHGTHVAGTIAALDNNVGVLGVAPDVDLFAVKVLGRSGSGSISGIAQGLQWSSNNNMD |
| Bacillus_okhensis_WP_034632645.1 | GNGHGTHVAGTIAALNNSIGVVGVAPNTELYAVKVLGANGSGSISSIAQGLQWTAQNNIH |
| B_gibsonii_AGS78407.1 | LNGHGTHVAGTVAALNNSIGVIGVAPNAELYAVKVLGANGSGSVSGIAQGLEWAATNNMH |
| B_lentus_P29600 | GNGHGTHVAGTIAALNNSIGVLGVAPSAELYAVKVLGASGSGSVSSIAQGLEWAGNNGMH |
| WO2015044206-0010 | GNGHGTHVAGTIAALDNSIGVLGVAPSAELYAVKVLGADGEGAISSIAQGLEWAGNNGMH |
| Bps02003 | LNGHGTHVAGTIAALNDGAGVIGVAPDAELYAVKVLGASGSGSVSSIAQGLEWAGDNGMD |
| B_pseudofirmus_ADC49870 | YNGHGTHVAGTVAALDNTTGVLGVAPSVSLYAVKVLDRNGSGSHASIAQGIEWAMNNGMD |
| B_licheniformis_CAJ70731.1 | GNGHGTHVAGTVAALDNSIGVLGVSYDVDLYAVKVLYAVKVLNSSGSGSYSGIVSGIEWATTNGMD |
| B_sp_sprD_AAC43581 | GNGHGTHVAGTVAALNNNVGVLGVAYNAELYAVKVLSAGGSGTLAGIAQGIEWAIDNNMD |
| Bacillus_sp_BAD11988 | SNGHGTHVAGTVAALNNTGVLGVLGVAYNADLYAVKVLSASGSGTLSGIAQGVEWSIANKMD |
| Bacillus_sp_sprC_AAC43580 | GNGHGTHVAGTVAALNNTTGVLGVAPSASLYAVKVLSASGSGTLSGIAQGIEWSISNGMN |
| B_amyloliquefaciens_CAA24990 | NNSHGTHVAGTVAALNNSIGVLGVAPSASLYAVKVLGADGSGQYSWINGIEWAIANNMD |
| B_atrophaeus_YP003972439 | GNSHGTHVAGTVAALNNSVGVLGVAPSASLYAVKVLSSSGSGDYSWINGIEWAISNNMD |

*FIG. 2B*

| | |
|---|---|
| BspAL03279 | IANLSLGSSAPSATLEQAVDEATANGVLVVAASGNSGAS------SIGYPARYDNAMAVGA |
| Bpan04382 | IANLSLGSSAPSATLEQAVDEATANGVLVVAASGNSGAS------SIGYPARYDNAMAVGA |
| BspAK01305 | VANLSLGSPSPSQTLEQAVNDATDSGVLVVAASGNSGTS------SLGYPARYDNAMAVGA |
| Bohn00569 | VANLSLGSPSPSQTLEQAVNDATDSGVLVVAAAGNSGTS------SLGYPARYDHAMAVGA |
| B.sp_B001_ADK62564.1 | VANLSLGSPSPSQTLEQAVNDATDSGVLVVAAAGNSGTS------SLGYPARYDNAMAVGA |
| Geomicrobium_sp_JCM19038_WP_042417589.1 | VANMSLGSPLPSPTLEQAVDEATDRGVLVVAASGNSGAS------SIGYPARYDNAMAVGA |
| Geomicrobium_sp_JCM_19055_WP_042358689.1 | VANMSLGSPLPSPTLEQAVDEATDRGVLVVAASGNSGAS------SLSYPAAYDNAMAVGA |
| Geomicrobium_sp_JCM_19037_WP_042398727.1 | VANMSLGSPSPSPTLERAVNQATNSGVLVVAASGNSGAS------SIGYPARYQNAMAVGA |
| Bacillus_okhensis_WP_034632645.1 | VANLSLGSPTGSQTLELAVNQATSAGVLVVAASGNNGSG------TISYPARYANALAVGA |
| B_gibsonii_AGS78407.1 | IANMSLGSDFFPSSTLERAVNYATSRDVLVIAATGNNGSG------SVGYPARYANAMAVGA |
| B_lentus_P29600 | VANLSLGSPSPSATLEQAVNSATSRGVLVVAASGNSGAG------SISYPARYANAMAVGA |
| WO2015044206-0010 | VANLSLGSPSPSATLEQAVNSATSRGVLVVAASGNSGAS------SIGYPARYANAMAVGA |
| Bps02003 | VANLSLGSPVGSDTLEQAVNYATDSGVLVVAASGNSGSG------TVSYPARYDNAFAVGA |
| B_pseudofirmus_ADC49870 | IANMSLGSPSGSTTLQLAADRARNAGVLLIGAAGNSGQQ--GGSNMGYPARYASVMAVGA |
| B_licheniformis_CAJ707311.1 | VINMSLGGASGSTAMKQAVDNAYARGVVVAAACNSGSS--GNTNTIGYPAKYDSVIAVGA |
| B_sp_sprD_AAC43581 | VINMSLGGSTGSTILKQASDNAYNSGIVVIAAAGNSGSVLGLVNTIGYPARYDSVIAVGA |
| Bacillus_sp_BAD11988 | VINMSLGGSSGSTALQRAVDNAYRNNIVVVAAAGNSGAQ--GNRNTIGYPARYSSVIAVGA |
| Bacillus_sp_sprC_AAC43580 | VINMSLGGSSGSTALQQACNNAYNGIVVIAAAGNSGSS--GNRNTMGYPARYSSVIAVGA |
| B_amyloliquefaciens_CAA24990 | VINMSLGGPSGSAALKAAVDKAVASGVVVAAAGNEGTS--GSSSTVGYPGKYPSVIAVGA |
| B_atrophaeus_YP003972439 | VINMSLGGPQGSTALKAVVDKAVSQGIVVVAAAGNSGSS--GSTSTVGYPAKYPSVIAVGA |

FIG. 2C

| | |
|---|---|
| BspAL03279 | TDQSDGLASFSQYGDGLDIVAPGVGIDSTYPGSSYDSLSGTSMATPHVAGAAALVKEKNP |
| Bpan04382 | TDQSDSLANFSQYGEGLDIVAPGVGIDSTYTGSSYDSLSGTSMATPHVAGSAALVKEKNP |
| BspAK01305 | TDQSDSLASFSQYGEGLDLVAPGVGIDSTYPGSSYDSLSGTSMAAPHVAGAAALVKQKNP |
| Bohn00569 | TDESDSLASFSQYGEGLDLVAPGVESTYPGGGYDSLSGTSMAAPHVAGAAALVKQKNP |
| B. sp_B001_ADK62564.1 | TDQSDSLASFSQYGEGLDLVAPGVESTYPGGGYDSLSGTSMAAPHVAGAAALVKQKNP |
| Geomicrobium_sp_JCM19038_WP_042417589.1 | TTQNDTRASFSQYGAGLDIVAPGVESTYPGGGYRSLDGTSMAAPHVAGVAALVLEQNP |
| Geomicrobium_sp_JCM_19055_WP_042358689.1 | TQSDARASFSQYGAGLDIVAPGVESTYPGGGYRSLDGTSMATPHVAGVAALVLEQNP |
| Geomicrobium_sp_JCM_19037_WP_042398727.1 | TDQNNRASFSQFGTGLDIMAPGVGVQSTYPGNGYRSLSGTSMAAPHVAGVAALVMSNNP |
| Bacillus_okhensis_WP_034632645.1 | TDQNNRASFSQYGTGLNIVAPGVGVQSTYPGNRYASLSGTSMATPHVAGVAALVKQKNP |
| B_gibsonii_AGS78407.1 | TDQNNRRANFSQYGTGICIDIVAPGVNQSTYPGNRYVSMNGTSMATPHVAGAAALVKQRYP |
| B_lentus_P29600 | TDQNNNRASFSQYGAGLDIVAPGVNVQSTYPGSTYASLNGTSMATPHVAGAAALILSKHP |
| WO2015044206-0010 | TDQNNRASFSRYGAGLDIVAPGVNVQSTYPGSTYASLNGTSMATPHVAGAAALVKQKNP |
| Bps02003 | TDQVNNRASFSQYGTGLDIVAPGVEVESTYLNGEYASLSGTSMATPHVAGVAALIKAKNP |
| B_pseudofirmus_ADC49870 | VDQNGNRANFSSYGSELEIMAPGVNINSTYLNNGYRSLNGTSMASPHVAGVAALVKQKHP |
| B_licheniformis_CAJ70731.1 | VDSNSNRASFSSVGAELEVMAPGAGVYSTYPTNTYATLNGTSMASPHVAGAAALILSKHP |
| B_sp_sprD_AAC43581 | VDSNNNRASFSSVGSQLEVMAPGVAINSTLPGNQYGELNGTSMASPHVAGAAALLLAQNP |
| Bacillus_sp_BAD11988 | VDSNNNRASFSSVGSELEVMAPGVSILSTVPGSSYASYNGTSMASPHVAGAAALLKAKYP |
| Bacillus_sp_sprC_AAC43580 | VSSNNTRASFSSVGSELEVMAPGVNILSTTPGNNYASFNGTSMAAPHVAGAAALIKAKHP |
| B_amyloliquefaciens_CAA24990 | VDSSNQRASFSSVGPELDVMAPGVSIQSTLPGNKYGAYNGTSMASPHVAGAAALILSKHP |
| B_atrophaeus_YP003972439 | VDSNNQRASFSSAGSELDVMAPGVSIQSTLPGSSYGSYNGTSMASPHVAGAAALVLSKHP |

*FIG. 2D*

| Name | Sequence | SEQ ID |
|---|---|---|
| BspAL03279 | LWSNEQIRAHLNETATDLGDMYRFGNGLLNAHAAVE | SEQ ID NO:27 |
| Bpan04382 | LWSNEQIRAHLNETATDLGDTYRFGNGLLNAHAAVE | SEQ ID NO:28 |
| BspAK01305 | GWTNEQIRSHLNDTANDLGDSFRFGSGLLNAENAVQ | SEQ ID NO:29 |
| Bohn00569 | SWTNEQIRGHLNDTANDLGDSFRFGSGLLNVENAVQ | SEQ ID NO:30 |
| B.sp_B001_ADK62564.1 | GWTNEQIRSHLNDTANDLGDSFRFGSGLLNAENAVQ | SEQ ID NO:31 |
| Geomicrobium_sp._JCM19038_WP_042417589.1 | SWSPQQVRNHLNDTATDLGDSNQYGSGLVDAVSATE | SEQ ID NO:32 |
| Geomicrobium_sp._JCM_19055_WP_042358689.1 | SWSPQQVRSHIVNDTATDLGDTNQPGSGLVDAESATD | SEQ ID NO:33 |
| Geomicrobium_sp._JCM_19037_WP_042398727.1 | SWSPAQVRSHLNQTATPIGASNQYGNGLVNANAATQ | SEQ ID NO:34 |
| Bacillus_okhensis_WP_034632645.1 | GWSNTQIRQHLLNTATPLGSSNQYGSGLVNAEAATR | SEQ ID NO:35 |
| B_gibsonii_AGS78407.1 | SWNATQIRNHLKNTATNLGNSSQFGSGLVNAEAATR | SEQ ID NO:36 |
| B_lentus_P29600 | SWSNVQIRNHLKNTATSLGSTNLYGSGLVNAEAATR | SEQ ID NO:37 |
| WO2015044206-0010 | SWSNVQIRNHLKNTATSLGDTNLYGSGLVNAEAATR | SEQ ID NO:38 |
| Bps02003 | MLSNEEIRQQLVQTATPLGSADMYGSGLVNAEVAVQ | SEQ ID NO:39 |
| B_pseudofirmus_ADC49870 | IILTAAQIRNRMNQTAIPLGNSTYYGNGLVDAEYAAQ | SEQ ID NO:40 |
| B_licheniformis_CAJ70731.1 | NLSASQVRNRLSSTATYLGSSFYYGKGLINVEAAAQ | SEQ ID NO:41 |
| B_sp_sprD_AAC43581 | NLTNVQVRERLRDTATNLGSAFNYGHGVINLERALQ | SEQ ID NO:42 |
| Bacillus_sp_BAD11988 | NWSAAQIRNKLSTTYLGSSFYYGNGVINVERALQ | SEQ ID NO:43 |
| Bacillus_sp_sprC_AAC43580 | SMTNVQIRERLKNTATNLGDPFFYGKGVINVESALQ | SEQ ID NO:44 |
| B_amyloliquefaciens_CAA24990 | NWTNTQVRSSLENTTKLGDSFYYGKGLINVQAAAQ | SEQ ID NO:45 |
| B_atrophaeus_YP003972439 | NWTNSQVRNSLESTATNLGNSFYYGKGLINVQAAAQ | SEQ ID NO:46 |

FIG. 2E

SERINE PROTEASES

This application is a Divisional of U.S. application Ser. No. 17/336,647, filed Jun. 2, 2021, which is a Continuation of U.S. application Ser. No. 15/884,749, filed Jan. 31, 2018, which is a Continuation of U.S. application Ser. No. 15/521,386, filed Apr. 24, 2017, which is a 371 of International Application No. PCT/US15/57526, filed Oct. 27, 2015 and claims the benefit of priority from U.S. Provisional Application No. 62/069,184 filed Oct. 27, 2014, all of which are herein incorporated by reference in their entirety.

REFERENCE TO SEQUENCE LISTING SUBMITTED ELECTRONICALLY

The official copy of the sequence listing is submitted electronically via Patent Center as an XML formatted sequence listing with a file named NB40679USPCD2_sequencelisting.xml created on Mar. 25, 2024 and having a size of 74,193 bytes and is filed concurrently with the specification. The sequence listing contained in this XML formatted document is part of the specification and is herein incorporated by reference in its entirety.

The present disclosure relates to serine proteases cloned from *Bacillus* spp., and variants thereof. Compositions containing the serine proteases are suitable for use in cleaning fabrics and hard surfaces, as well as in a variety of industrial applications.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

The present compositions and methods relate to recombinant serine proteases cloned from *Bacillus* spp., and variants thereof. Compositions containing the serine proteases are suitable for use in cleaning fabrics and hard surfaces, as well as in a variety of industrial applications.

In some embodiments, the invention is a BspAL03279-clade of subtilisins. The BspAL03279-clade of subtilisins is characterized by a common motif over the sequence that begins with Aspartic acid (D250) and ends at position 269, according to BspAL03279 numbering. In some embodiments, the invention is a recombinant polypeptide or active fragment thereof of a BspAL03279-clade subtilisin. In further embodiments, the BspAL03279-clade of subtilisins comprises a subtilisin or recombinant polypeptide or active fragment thereof comprising a DLGDXXRFGX$_a$GL-LXXXXAVX (SEQ ID NO:26) motif, wherein X is any amino acid and X$_a$ is N or S ("Motif 1"). In yet further embodiments, the BspAL03279-clade of subtilisins comprises a subtilisin or recombinant polypeptide or active fragment thereof comprising a DLGDXXRFGX$_a$GL-LXXXXAVX (SEQ ID NO:26) motif, wherein X is any amino acid and X$_a$ is N ("Motif 2"). In yet still further embodiments, the BspAL03279-clade of subtilisins comprises a subtilisin or recombinant polypeptide or active fragment thereof comprising a DLGDXXRFGX$_a$GL-LXXXXAVX (SEQ ID NO:26) motif, wherein X is any amino acid and X$_a$ is S ("Motif 3").

In some embodiments, the invention is a recombinant polypeptide or active fragment thereof comprising an amino acid sequence having at least 70% or 80% identity to an amino acid sequence selected from the group consisting of SEQ ID NOs: 3, 6, 9, 12, and 15. In some embodiments, the recombinant polypeptide has cleaning activity in a detergent composition, including an automatic dish washing detergent and a laundry detergent.

In some embodiments, the invention is a composition comprising a surfactant and the recombinant polypeptide stated above. In some embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the composition is a detergent composition, such as a laundry detergent, a fabric softening detergent, a dishwashing detergent, and a hard-surface cleaning detergent. In some embodiments, the composition further comprises at least one calcium ion and/or zinc ion, at least one stabilizer, at least one bleaching agent, phosphate, or borate. In some embodiments the composition is phosphate-free and/or borate-free. In some embodiments, the composition is a granular, powder, solid, bar, liquid, tablet, gel, paste or unit dose composition. In some embodiments, the composition further comprising one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

In some embodiments, the invention is a method of cleaning, comprising contacting a surface or an item with a composition listed above. In some embodiments, the invention is a method for producing a recombinant polypeptide comprising stably transforming a host cell with an expression vector comprising a polynucleotide encoding the recombinant polypeptide above.

BRIEF DESCRIPTION OF THE DRAWINGS

FIG. 2A-E provides MUSCLE multiple sequence alignment of subtilisins including BspAL03279, BspAK01305, Bps02003, Bohn00569, and Bpan04382.

Figure 1:
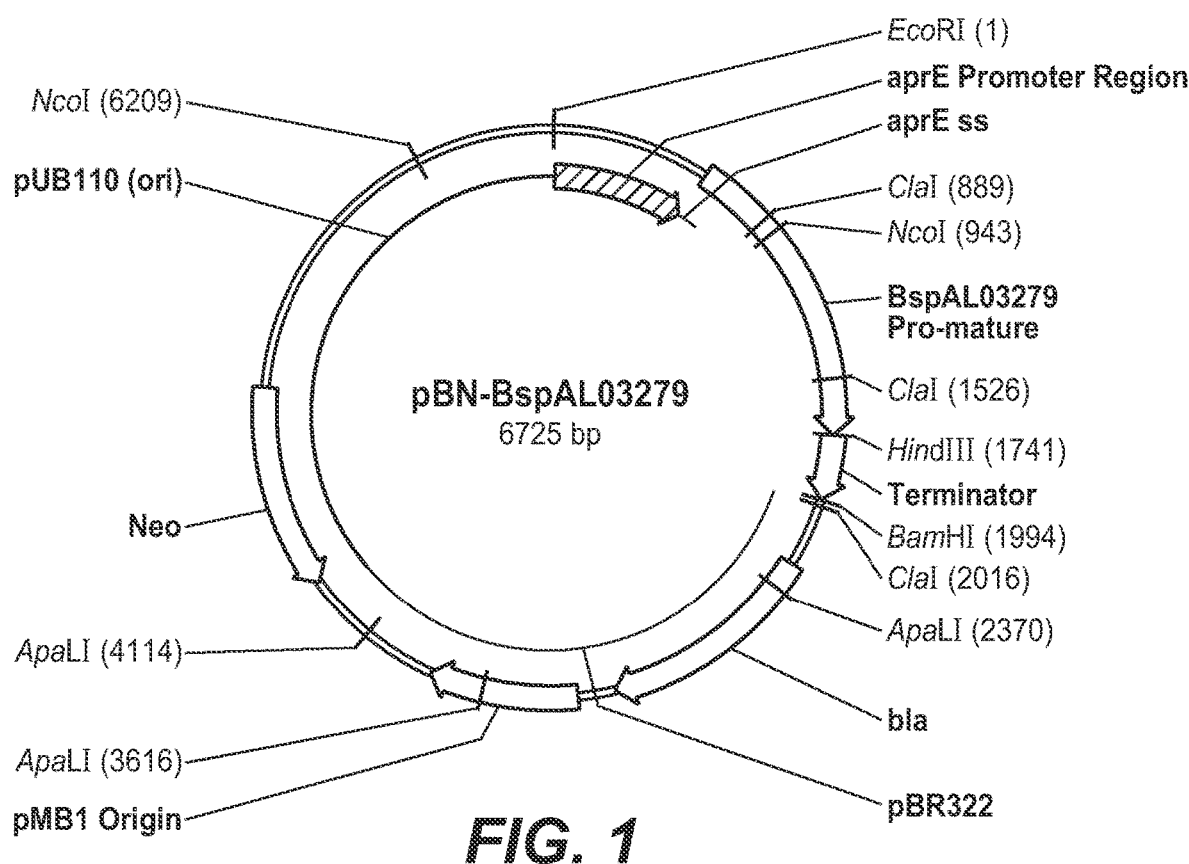
FIG. 1 provides a plasmid map for expression of BspAL03279 protease.

Described are compositions and methods relating to recombinant serine proteases from *Bacillus* species. The compositions and methods are based, in part, on the observation that recombinant BspAL03279, BspAK01305, Bps02003, Bohn00569, and Bpan04382, among others, have protease activity in the presence of a surfactant, in basic reaction conditions, and at elevated temperatures. These features of BspAL03279, BspAK01305, Bps02003, Bohn00569, and Bpan04382 make these proteases well suited for use in cleaning fabrics and hard surfaces, as well as in textile, leather and feather processing. The new proteases are also well suited to inclusion in compositions for protein degradation, including but not limited to laundry and dish washing detergents.

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S.

Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii,* and *B. thuringiensis*. It is recognized that the genus *Bacillus* continues to undergo taxonomical reorganization. Thus, it is intended that the genus include species that have been reclassified, including but not limited to such organisms as *Bacillus stearothermophilus*, which is now named "*Geobacillus stearothermophilus*", or *Bacillus polymyxa*, which is now "*Paenibacillus polymyxa*" The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms described below and known in the art.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001 (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Another useful algorithm for comparison of multiple protein sequences is the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797).

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The present disclosure provides novel serine protease enzymes. The serine protease polypeptides of the present disclosure include isolated, recombinant, substantially pure, or non-naturally occurring polypeptides. In some embodiments, the polypeptides are useful in cleaning applications and can be incorporated into cleaning compositions that are useful in methods of cleaning an item or a surface in need thereof.

In some embodiments, the invention is a BspAL03279-clade of subtilisins. In other embodiments, the invention is a recombinant polypeptide or active fragment thereof of a BspAL03279-clade subtilisin. In further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is N or S ("Motif 1"). In yet further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is N ("Motif 2"). In yet still further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is S ("Motif 3").

In still further embodiments, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is N or S, with the proviso that the subtilisin or recombinant polypeptide or active fragment thereof does not comprise ADK62564. In an even further embodiment, the BspAL03279-clade of subtilisins comprises a subtilisin or recombinant polypeptide or active fragment thereof comprising a DLGDXXRFGX$_a$GLLXXXXAVX (SEQ ID NO:26) motif, wherein X is any amino acid and X$_a$ is S, with the proviso that the subtilisin or recombinant polypeptide or active fragment thereof does not comprise ADK62564.

In some embodiments, the polypeptide of the present invention is a polypeptide having a specified degree of amino acid sequence homology to the exemplified polypeptides, e.g., 70%, 75%, 80%, 85%, 90%, 95%, 96%, 97%, 98%, 99% or 100% amino acid sequence identity to an amino acid sequence selected from the group consisting of SEQ ID NOs:3, 6, 9, 12, and 15. In other embodiments, the recombinant polypeptide or active fragment thereof comprises an amino acid sequence having at least 75% amino acid sequence identity to an amino acid sequence of SEQ ID NO:6 or 12, with the proviso that the recombinant polypeptide or active fragment thereof does not comprise ADK62564. In other embodiments, the recombinant polypeptide or active fragment thereof comprises an amino acid sequence having at least 80% amino acid sequence identity to an amino acid sequence selected from the group consisting of SEQ ID NOs: 3, 9, and 15. In other embodiments, the recombinant polypeptide or active fragment thereof comprises an amino acid sequence having at least 80% amino acid sequence identity to an amino acid sequence selected from the group consisting of SEQ ID NOs: 3, 6, 9, 12, and 15, with the proviso that the recombinant polypeptide or active fragment thereof does not comprise ADK62564 or optionally WP_035392836, WP_038476582, WP_035392836 or WP_047989534. In other embodiments, the recombinant polypeptide or active fragment thereof comprises an amino acid sequence having at least 97% amino acid sequence identity to an amino acid sequence selected from the group consisting of SEQ ID NOs: 3, 9, 12, and 15.

Homology can be determined by amino acid sequence alignment, e.g., using a program such as BLAST, ALIGN, MUSCLE, or CLUSTAL, as described herein. In some embodiments, the polypeptide is an isolated, recombinant, substantially pure, or non-naturally occurring enzyme having protease activity, such as subtilisin activity, or casein hydrolysis activity (for example, dimethylcasein hydrolysis activity).

Also provided is a polypeptide enzyme of the present invention, having protease activity, such as alkaline protease activity, said enzyme comprising an amino acid sequence which differs from the amino acid sequence of SEQ ID NOs:3, 6, 9, 12, and 15 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant serine protease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples.

The serine protease polypeptides of the present invention can have protease activity over a broad range of pH conditions. In some embodiments, the serine protease polypeptides have protease activity on dimethylcasein as a substrate, as demonstrated in Examples below.

In some embodiments, the serine protease polypeptides of the present invention demonstrate cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the serine protease polypeptides of the present invention demonstrate cleaning performance in automatic dishwashing (ADW) detergent compositions. In some embodiments, the cleaning performance in ADW detergent compositions includes cleaning of egg yolk stains. In some embodiments, the serine protease polypeptides of the present invention demonstrate cleaning performance in laundry detergent compositions. In some embodiments, the cleaning performance in laundry detergent compositions includes cleaning of blood/milk/ink stains. In each of the cleaning compositions, the serine protease polypeptides of the present invention demonstrate cleaning performance with or without a bleach component.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include serine protease polypeptides having enzymatic activity (e.g., proteolytic activity) which are useful in cleaning applications and cleaning compositions for cleaning an item or a surface (e.g., surface of an item) in need of cleaning.

In some embodiments, the polynucleotide of the present invention is a polynucleotide having a specified degree of nucleic acid homology to the exemplified polynucleotide. In some embodiments, the polynucleotide comprises a nucleic acid sequence having at least 50, 60, 65, 70, 75, 80, 85, 90, 91, 92, 93, 94, 95, 96, 97, 98, 99 or 100% identity to the nucleic acid sequence of SEQ ID NOs:1, 4, 7, 10, 13, 16, 18, 20, 22, or 24. In some embodiments, the polynucleotide comprises a nucleic acid sequence selected from the group consisting of SEQ ID NOs:1, 4, 7, 10, 13, 16, 18, 20, 22, and 24. In other embodiments, the polynucleotide may also have a complementary nucleic acid sequence to a nucleic acid sequence selected from the group consisting of SEQ ID NOs:1, 4, 7, 10, 13, 16, 18, 20, 22, and 24. In some embodiments, the polynucleotide comprises a nucleic acid sequence encoding a recombinant polypeptide or an active fragment thereof, comprising an amino acid sequence having at least 70, 75, 80, 85, 90, 95, 96, 97, 98, 99, or 100% amino acid identity to an amino acid sequence selected from the group consisting of SEQ ID NOs: 3, 6, 9, 12, and 15. In some embodiments, the polynucleotide comprises a nucleic acid sequence encoding a recombinant polypeptide or an active fragment thereof, comprising an amino acid sequence selected from the group consisting of SEQ ID NOs:3, 6, 9, 12, and 15. Homology can be determined by amino acid sequence alignment, e.g., using a program such as BLAST, ALIGN, MUSCLE, or CLUSTAL, as described herein.

In some embodiments, the invention provides an isolated, recombinant, substantially pure, synthetically derived, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, synthetically derived, or non-naturally-occurring nucleic acid comprising a nucleotide sequence encoding a combination of two or more of any polypeptides of the invention described above and elsewhere herein. The present invention provides nucleic acids encoding a serine protease polypeptide of the present invention, wherein the serine protease polypeptide is a mature form having proteolytic activity. In some embodiments, the serine protease is expressed recombinantly with a homologous pro-peptide sequence. In other embodiments, the serine protease is expressed recombinantly with a heterologous pro-peptide sequence (e.g., GG36 pro-peptide sequence.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a serine protease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides of the invention that encode serine protease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

The present invention provides vectors comprising at least one serine protease polynucleotide of the invention described herein (e.g., a polynucleotide encoding a serine protease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector, although other methods are available and known in the art. Such cells are typically referred to as host cells. Some such cells comprise bacterial cells, including, but are not limited to Bacillus sp. cells, such as B. subtilis cells. The invention also provides recombinant cells (e.g., recombinant host cells) comprising at least one serine protease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a serine protease polypeptide of the invention is operably linked to one or additional nucleic acid segments required for efficient gene expression (e.g., a promoter operably linked to the polynucleotide of the invention which encodes a serine protease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments of the present invention, a polynucleotide sequence encoding the serine protease polypeptide (as well as other sequences included in the vector) is integrated into the genome of the host cell, while in other embodiments, a plasmid vector comprising a polynucleotide sequence encoding the serine protease polypeptide remains as autonomous extrachromosomal element within the cell. The invention provides both extrachromosomal nucleic acid elements as well as incoming nucleotide sequences that are integrated into the host cell genome. The vectors described herein are useful for production of the serine protease polypeptides of the invention. In some embodiments, a polynucleotide construct encoding the serine protease polypeptide is present on an integrating vector that enables the integration and optionally the amplification of the polynucleotide encoding the serine protease polypeptide into the host chromosome. Examples of sites for integration are well known to those skilled in the art. In some embodiments, transcription of a polynucleotide encoding a serine protease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda PR or PL promoters, and the *E. coli* lac, trp or tac promoters.

Serine protease polypeptides of the present invention can be produced in host cells of any suitable microorganism, including bacteria and fungi. In some embodiments, serine protease polypeptides of the present invention can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the serine protease polypeptides are produced by *Bacillus* sp. host cells. Examples of *Bacillus* sp. host cells that find use in the production of the serine protease polypeptides of the invention include, but are not limited to *B. licheniformis*, *B. lentus*, *B. subtilis*, *B. amyloliquefaciens*, *B. lentus*, *B. brevis*, *B. stearothermophilus*, *B. alkalophilus*, *B. coagulans*, *B. circulans*, *B. pumilis*, *B. thuringiensis*, *B. clausii*, and *B. megaterium*, as well as other organisms within the genus *Bacillus*. In some embodiments, *B. subtilis* host cells are used for production of serine protease polypeptides. U.S. Pat. Nos. 5,264,366 and 4,760,025 (RE 34,606) describe various *Bacillus* host strains that can be used for producing serine protease polypeptide of the invention, although other suitable strains can be used.

Several bacterial strains that can be used to produce serine protease polypeptides of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, M1113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a serine protease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., US 2005/0202535, incorporated herein by reference).

Host cells are transformed with at least one nucleic acid encoding at least one serine protease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087

[1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a serine protease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one serine protease polypeptide or at least one nucleic acid of the invention.

In some embodiments, host cells transformed with at least one polynucleotide sequence encoding at least one serine protease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

Assays for detecting and measuring the enzymatic activity of an enzyme, such as a serine protease polypeptide of the invention, are well known. Various assays for detecting and measuring activity of proteases (e.g., serine protease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature serine protease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature serine protease polypeptide of the invention. A mature serine protease polypeptide does not include a signal peptide or a propeptide sequence. Some methods comprise making or producing a serine protease polypeptide of the invention in a recombinant bacterial host cell, such as for example, a *Bacillus* sp. cell (e.g., a *B. subtilis* cell). In some embodiments, the invention provides a method of producing a serine protease polypeptide of the invention, the method comprising cultivating a recombinant host cell comprising a recombinant expression vector comprising a nucleic acid encoding a serine protease polypeptide of the invention under conditions conducive to the production of the serine protease polypeptide. Some such methods further comprise recovering the serine protease polypeptide from the culture.

In some embodiments the invention provides methods of producing a serine protease polypeptide of the invention, the methods comprising: (a) introducing a recombinant expression vector comprising a nucleic acid encoding a serine protease polypeptide of the invention into a population of cells (e.g., bacterial cells, such as *B. subtilis* cells); and (b) culturing the cells in a culture medium under conditions conducive to produce the serine protease polypeptide encoded by the expression vector. Some such methods further comprise: (c) isolating the serine protease polypeptide from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, antioxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101 all of which are incorporated herein by reference. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

The serine protease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the serine protease polypeptides provided herein, alone or in combination with other proteases and/or additional enzymes. The required level of enzyme is achieved by the addition of one or more serine protease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the serine protease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when the serine protease polypeptide (s) is/are employed in a granular composition or liquid, it is desirable for the serine protease polypeptide to be in the form of an encapsulated particle to protect the serine protease polypeptide from other components of the granular composition during storage. In addition, encapsulation is also a means of controlling the availability of the serine protease polypeptide during the cleaning process. In some embodiments, encapsulation enhances the performance of the serine protease polypeptide (s) and/or additional enzymes. In this regard, the serine protease polypeptides of the present invention are encapsulated with any suitable encapsulating material known in the art. In some embodiments, the encapsulating material typically encapsulates at least part of the serine protease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM6545, PM6550, PM7220, PM7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components is present in the wash water. A medium detergent concentration includes detergents where between about 800 ppm and about 2000 ppm of the detergent components is present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

TABLE I

Water Hardness

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Accordingly, in some embodiments, the present invention provides serine protease polypeptides that show surprising wash performance in at least one set of wash conditions (e.g., water temperature, water hardness, and/or detergent concentration). In some embodiments, the serine protease polypeptides of the present invention are comparable in wash performance to other serine protease polypeptide proteases. In some embodiments of the present invention, the serine protease polypeptides provided herein exhibit enhanced oxidative stability, enhanced thermal stability, enhanced cleaning capabilities under various conditions, and/or enhanced chelator stability. In addition, the serine protease polypeptides of the present invention find use in cleaning compositions that do not include detergents, again either alone or in combination with builders and stabilizers.

In some embodiments of the present invention, the cleaning compositions comprise at least one serine protease polypeptide of the present invention at a level from about 0.00001 to about 10% by weight of the composition and the balance (e.g., about 99.999 to about 90.0%) comprising cleaning adjunct materials by weight of composition. In some other embodiments of the present invention, the cleaning compositions of the present invention comprises at least one serine protease polypeptide at a level of about 0.0001 to about 10%, about 0.001 to about 5%, about 0.001 to about 2%, about 0.005 to about 0.5% by weight of the composition and the balance of the cleaning composition (e.g., about 99.9999 to about 90.0%, about 99.999 to about 98%, about 99.995 to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the serine protease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606; 5,955,340; 5,700,676; 6,312,936; and 6,482,628, all of which are incorporated herein by reference. Additional protease examples include, but are not limited to trypsin (e.g., of porcine or bovine origin), and the *Fusarium* protease described in WO89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™ EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™ POLARZYME®, OVOZYME®, KANNASE®, LIQUANASE®, NEUTRASE®, RELASE® and ESPERASE® (Novozymes); BLAP™ and BLAP™ (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO92/21760, WO 09/149200, WO09/149144, WO09/149145, WO11/072099, WO10/056640, WO10/056653, WO 11/140364, WO12/151534, US 2008/0090747, and U.S. Pat. Nos. 5,801,039; 5,340,735; 5,500,364; 5,855,625; RE 34,606; 5,955,340; 5,700,676; 6,312,936; 6,482,628; 8,530,219; and various other patents. In some further embodiments, neutral metalloproteases find use in the present invention, including but not limited to the neutral metalloproteases described in WO1999014341, WO1999033960, WO 1999014342, WO1999034003, WO2007044993, WO2009058303, WO2009058661, WO 2014/071410, WO2014/194032, WO2014/194034, WO2014/194054, and WO2014/194117. Exemplary metalloproteases include nprE, the recombinant form of neutral metalloprotease expressed in *B. subtilis* (See e.g., WO07/044993), and PMN, the purified neutral metalloprotease from *B. amyloliquefaciens*.

In addition, any suitable lipase finds use in the present invention. Suitable lipases include, but are not limited to those of bacterial or fungal origin. Chemically or genetically modified mutants are encompassed by the present invention. Examples of useful lipases include *H. lanuginosa* lipase (See e.g., EP 258 068, and EP 305 216), *Rhizomucor miehei* lipase (See e.g., EP 238 023), *Candida* lipase, such as *C. antarctica* lipase (e.g., *C. antarctica* lipase A or B; See e.g., EP214761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO88/09367), and the cutinase derived from *Fusarium solani pisi* (See, WO90/09446).

Additional suitable lipases include lipases such as M1 LIPASE™, LUMA FAST™ and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001 to about 10% of additional lipase by weight of the composition and the balance of cleaning adjunct materials by weight of composition. In some other embodiments of the present invention, the cleaning compositions of the present invention also comprise lipases at a level of about 0.0001 to about 10%, about 0.001 to about 5%, about 0.001 to about 2%, about 0.005 to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Additional suitable amylases include those found in WO9510603, WO9526397, WO9623874, WO9623873, WO9741213, WO 9919467, WO0060060, WO0029560, WO9923211, WO9946399, WO0060058, WO0060059, WO9942567, WO0114532, WO02092797, WO0166712, WO0188107, WO0196537, WO 0210355, WO9402597, WO0231124, WO9943793, WO9943794, WO2004113551, WO 2005001064, WO2005003311, WO0164852, WO2006063594, WO2006066594, WO 2006066596, WO2006012899, WO2008092919, WO2008000825, WO2005018336, WO 2005066338, WO2009140504, WO2005019443, WO2010091221, WO2010088447, WO 0134784, WO2006012902, WO2006031554, WO2006136161, WO2008101894, WO 2010059413, WO2011098531, WO2011080352, WO2011080353, WO2011080354, WO 2011082425, WO2011082429, WO2011076123, WO2011087836, WO2011076897, WO 94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021. Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™ RAPIDASE® and MAXAMYL® P (Genencor).

In some embodiments of the present invention, the cleaning compositions of the present invention further comprise amylases at a level from about 0.00001 to about 10% of additional amylase by weight of the composition and the balance of cleaning adjunct materials by weight of composition. In some other embodiments of the present invention, the cleaning compositions of the present invention also comprise amylases at a level of about 0.0001 to about 10%, about 0.001 to about 5%, about 0.001 to about 2%, about 0.005 to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to H. insolens cellulases (See e.g., U.S. Pat. No. 4,435,307). Especially suitable cellulases are the cellulases having color care benefits (See e.g., EP0495257). Commercially available cellulases that find use in the present include, but are not limited to CELLUZYME®, CAREZYME® (Novozymes), REVITALENZ™ 100 (Danisco US Inc) and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, and U.S. Pat. Nos. 7,449,318 and 7,833,773. In some embodiments, the cleaning compositions of the present invention further comprise cellulases at a level from about 0.00001 to about 10% of additional cellulase by weight of the composition and the balance of cleaning adjunct materials by weight of composition. In some other embodiments of the present invention, the cleaning compositions of the present invention also comprise cellulases at a level of about 0.0001 to about 10%, about 0.001 to about 5%, about 0.001 to about 2%, about 0.005 to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114; 6,602,842; and 6,440,991, all of which are incorporated herein by reference). Commercially available mannanases that find use in the present invention include, but are not limited to MANNASTAR®, PURABRITE™, and MANNAWAY®. In some embodiments, the cleaning compositions of the present invention further comprise mannanases at a level from about 0.00001 to about 10% of additional mannanase by weight of the composition and the balance of cleaning adjunct materials by weight of composition. In some embodiments of the present invention, the cleaning compositions of the present invention also comprise mannanases at a level of about 0.0001 to about 10%, about 0.001 to about 5%, about 0.001 to about 2%, about 0.005 to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001 to about 10% of additional peroxidase and/or oxidase by weight of the composition and the balance of cleaning adjunct materials by weight of composition. In some other embodiments of the present invention, the cleaning compositions of the present invention also comprise peroxidase and/or oxidase enzymes at a level of about 0.0001 to about 10%, about 0.001 to about 5%, about 0.001 to about 2%, about 0.005 to about 0.5% peroxidase and/or oxidase enzymes by weight of the composition.

In some embodiments, additional enzymes find use, including but not limited to perhydrolases (See e.g., WO 2005056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the serine protease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more serine protease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the serine protease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the serine protease polypeptides of the present invention. Thus, in some embodiments, the compositions comprising at least one serine protease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one serine protease polypeptide of the present invention are fabric cleaning compositions such as those described in U.S. Pat. Nos. 6,610,642 and 6,376,450. In addition, the serine protease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one serine protease polypeptide provided herein. Thus, in some embodiments, the compositions comprising at least one serine protease polypeptide of the present invention is a hard surface cleaning composition such as those described in U.S. Pat. Nos. 6,610,642; 6,376,450; and 6,376,450.

In yet further embodiments, the present invention provides dishwashing compositions comprising at least one serine protease polypeptide provided herein. Thus, in some embodiments, the compositions comprising at least one serine protease polypeptide of the present invention is a hard surface cleaning composition such as those in U.S. Pat. Nos. 6,610,642 and 6,376,450. In some still further embodiments, the present invention provides dishwashing compositions comprising at least one serine protease polypeptide provided herein. In some further embodiments, the compositions comprising at least one serine protease polypeptide of the present invention comprise oral care compositions such as those in U.S. Pat. Nos. 6,376,450 and 6,376,450. The formulations and descriptions of the compounds and cleaning adjunct materials contained in the aforementioned U.S. Pat. Nos. 6,376,450; 6,605,458; 6,605,458; and 6,610,642, find use with the serine protease polypeptides provided herein.

The cleaning compositions of the present invention are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303, all of which are incorporated herein by reference. When a low pH cleaning composition is desired, the pH of such composition is adjusted via the addition of a material such as monoethanolamine or an acidic material such as HCl.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyl-iminodiacetic acid (MIDA), alpha-alanine-N,N-diacetic acid (alpha-ALDA), serine-N,N-diacetic acid (SEDA), iso-serine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3 to about 60% or even from about 5 to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3, 5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1 to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1 to about 15% or even from about 3.0 to about 10% chelating agent by weight of the subject cleaning composition.

In some still further embodiments, the cleaning compositions provided herein contain at least one deposition aid. Suitable deposition aids include, but are not limited to, polyethylene glycol; polypropylene glycol; polycarboxylate; soil release polymers such as polytelephthalic acid, clays such as kaolinite, montmorillonite, atapulgite, illite, bentonite, and halloysite; and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2100949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001 to about 10%, from about 0.01 to about 5%, or even from about 0.1 to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1 to about 20%. In some embodiments, silicates are present at a level of from about 5 to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleach, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP2100949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP2100949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612; 5,227,084; 4,810,410; WO99/06521; and EP2100949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 to about 25 ppm, more preferably from about 0.05 to about 10 ppm, and most preferably from about 0.1 to about 5 ppm of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP2100949, WO9426860 and WO94/26859). In some embodiments, the metal care agent is a zinc salt. In some further embodiments, the cleaning compositions of the present invention comprise from about 0.1 to about 5% by weight of one or more metal care agent.

In some embodiments, the cleaning composition is a high density liquid (HDL) composition having a variant serine protease polypeptide protease. The HDL liquid laundry detergent can comprise a detersive surfactant (10-40%) comprising anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$alkyl ethoxylated alcohol and/or $C_6$-$C_{12}$alkyl phenol alkoxylates), optionally wherein the weight ratio of anionic detersive surfactant (with a hydrophilic index (HIc) of from 6.0 to 9) to non-ionic detersive surfactant is greater than 1:1.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 to 10 wt %); deposition aids (examples for which include polysaccharides, preferably cellulosic polymers, poly diallyl dimethyl ammonium halides (DADMAC), and co-polymers of DADMAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can be any liquid form, for example a liquid or gel form, or any combination thereof. The composition may be in any unit dose form, for example a pouch.

In some embodiments, the cleaning composition is a high density powder (HDD) composition having a variant serine protease polypeptide protease. The HDD powder laundry detergent can comprise a detersive surfactant including anionic detersive surfactants (selected from a group of linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from a group of linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from a group of alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (selected from a group of alkanolamine sulpho-betaines); ampholytic surfactants; semi-polar non-ionic surfactants and mixtures thereof; builders (phosphate free builders [for example zeolite builders examples of which include zeolite A, zeolite X, zeolite P and zeolite MAP in the range of 0 to less than 10 wt %]; phosphate builders [examples of which include sodium tri-polyphosphate in the range of 0 to less than 10 wt %]; citric acid, citrate salts and nitrilotriacetic acid or salt thereof in the range of less than 15 wt %); silicate salt (sodium or potassium silicate or sodium meta-silicate in the range of 0 to less than 10 wt %, or layered silicate (SKS-6)); carbonate salt (sodium carbonate and/or sodium bicarbonate in the range of 0 to less than 10 wt %); and bleaching agents (photobleaches, examples of which include sulfonated zinc phthalocyanines, sulfonated aluminum phthalocyanines, xanthenes dyes, and mixtures thereof; hydrophobic or hydrophilic bleach activators (examples of which include dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof; hydrogen peroxide; sources of hydrogen peroxide (inorganic perhydrate salts examples of which include mono or tetra hydrate sodium salt of perborate, percarbonate, persulfate, perphosphate, or persilicate); preformed hydrophilic and/or hydrophobic peracids (selected from a group consisting of percarboxylic acids and salts, percarbonic acids and salts, perimidic acids and salts, peroxymonosulfuric acids and salts) & mixtures thereof and/or bleach catalyst (such as imine bleach boosters examples of which include iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; metal-containing bleach catalyst for example copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of poly-carboxylic acids and their partially or completely neutralized salts, monomeric polycarboxylic acids and hydroxycarboxylic acids and their salts in the range of 0.5 to 50% by weight; sulfonated/carboxylated polymers (provide dimensional stability to the product) in the range of about 0.1 to about 50% by weight; drying aids in the range of about 0.1 to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators—organic peracid precursors in the range from about 0.1 to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1 to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

In some embodiments, the cleaning composition is borate-free. In some embodiments, the cleaning composition is phosphate-free.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001 to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

Also provided are compositions and methods of treating fabrics (e.g., to desize a textile) using a serine protease polypeptide of the present invention. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

A serine protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A serine protease of the present invention can be applied during or after the weaving to remove the sizing starch or starch derivatives. After weaving, the serine protease can be used to remove the size coating before further processing the fabric to ensure a homogeneous and wash-proof result.

A serine protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

The serine protease polypeptides described herein find further use in the enzyme aided removal of proteins from animals and their subsequent degradation or disposal, such as feathers, skin, hair, hide, and the like. In some instances, immersion of the animal carcass in a solution comprising a serine protease polypeptide of the present invention can act to protect the skin from damage in comparison to the traditional immersion in scalding water or the defeathering process. In one embodiment, feathers can be sprayed with an isolated serine protase polypeptide of the present invention under conditions suitable for digesting or initiating degradation of the plumage. In some embodiments, a serine protease of the present invention can be used, as above, in combination with an oxidizing agent.

In some embodiments, removal of the oil or fat associated with raw feathers is assisted by using a serine protease polypeptide of the present invention. In some embodiments, the serine protease polypeptides are used in compositions for cleaning the feathers as well as to sanitize and partially dehydrate the fibers. In yet other embodiments, the disclosed serine protease polypeptides find use in recovering protein from plumage. In some other embodiments, the serine protease polypeptides are applied in a wash solution in combination with 95% ethanol or other polar organic solvent with or without a surfactant at about 0.5% (v/v).

In a further aspect of the invention, the serine protease polypeptides of the present invention can be used as a component of an animal feed composition, animal feed additive and/or pet food comprising a serine protease and variants thereof. The present invention further relates to a method for preparing such an animal feed composition, animal feed additive composition and/or pet food comprising mixing the serine protease polypeptide with one or more animal feed ingredients and/or animal feed additive ingredients and/or pet food ingredients. Furthermore, the present invention relates to the use of the serine protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and e) minerals and vitamins.

The protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a protease polypeptide of the present invention under conditions suitable for bleaching the paper pulp.

In some embodiments, the pulps are chlorine free pulps bleached with oxygen, ozone, peroxide or peroxyacids. In some embodiments, the protease polypeptides are used in enzyme aided bleaching of pulps produced by modified or continuous pulping methods that exhibit low lignin contents. In some other embodiments, the protease polypeptides are applied alone or preferably in combination with xylanase and/or endoglucanase and/or alpha-galactosidase and/or cellobiohydrolase enzymes.

The protease polypeptides described herein find further use in the enzyme aided removal of proteins from animals and their subsequent degradation or disposal, such as feathers, skin, hair, hide, and the like. In some instances, immersion of the animal carcass in a solution comprising a protease polypeptide of the present invention can act to protect the skin from damage in comparison to the traditional immersion in scalding water or the defeathering process. In one embodiment, feathers can be sprayed with an isolated protease polypeptide of the present invention under conditions suitable for digesting or initiating degradation of the plumage. In some embodiments, a protease of the present invention can be used, as above, in combination with an oxidizing agent.

In some embodiments, removal of the oil or fat associated with raw feathers is assisted by using a protease polypeptide of the present invention. In some embodiments, the protease polypeptides are used in compositions for cleaning the feathers as well as to sanitize and partially dehydrate the fibers. In some other embodiments, the protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

EXAMPLES

The following examples are provided to demonstrate and illustrate certain preferred embodiments and aspects of the present disclosure and should not be construed as limiting. In the experimental disclosure which follows, the following abbreviations apply: ADW (automatic dish washing); BMI (blood/milk/ink); BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); and w/v (weight to volume).

Example 1

Discovery and Identification of *Bacillus* Serine Proteases

*Bacillus* sp. DSM 8714, *Bacillus* sp. DSM 8717, *B. pseudalcaliphilus* DSM 8725, *B. oshimensis* NCIMB 14023, and *B. patagoniensis* DSM 16117, were all selected as a potential source for enzymes useful in industrial applications. The DSM strains were obtained from Leibniz-Institut DSMZ—Deutsche Sammlung von Mikroorganismen und Zellkulturen GmbH. *Bacillus oshimensis* NCIMB 14023 was obtained from NCIMB Ltd, Aberdeen, Scotland. WDG290 and WDG291 are from the Dupont Culture Collection.

To identify enzymes produced by these strains and the genes that encode these enzymes, the genomes of these strains were sequenced using Illumina® sequencing by synthesis (SBS) technology. Genome sequencing and assembly of the sequence data was performed by BaseClear (Leiden, The Netherlands). Contigs were annotated by BioXpr (Namur, Belgium). One of genes identified this way in strain *Bacillus* sp. DSM 8714 encodes a protein that shows homology to serine proteases of various other bacteria. The sequence of this gene, BspAL03279.n, is depicted in SEQ ID NO:1.

SEQ ID NO: 1 sets forth the nucleotide sequence of the BspAL03279.n gene: ATGA ATCGAAAACCAGTTA AACTAATCGCAGGAACAGCTCTTGTTATGGGCTT TGTCATCA GTTCATCATCCATATCAACTGCCGAGGA AACAAAAAAGACTTATCTTATTGGCTTTG ATGCT CAGGAAGAAGTCGAAACATTCACGAATATGGTC-GATTCTGAGATAGGGGCT CTATCTGAAGAAGAAAT-TGATATTACCTACGAATTTAAAGAAATACCGG TCG TCTCT GCTGAAATGAGTGAAGAAGAATATGCAG-CATTACTAGAAGACCCATCGATATCATA TATTGAA GAAGACATCGAAGTAACAACAATGGCCCAAGCC ATTCCATGGGGAATTA GTCAAATTAGTGCCCCTGA AGCGCAAATTGCTGGATTTACTGGTGAGGGTGTA AATG TTGCGGTGCTGGATACTGGAATAGAGGATCA CCCCGATTTAAACGTTCAAGGCGGTG TTAGCTTT G TTCAAGGAGAGCCGGATTATCAGGATGGAAATGG ACACGGAACCCAT GTCGCCGGTACAATCGCT GC CCTTGATAACGACGAAGGCGTAATTGGAGT CGC ACC AAATGCAGATCTTTATGCAGTCAAAGTTCTGG TG CAAATGGTTCTGGCTCAGTCAG CTCAATTGCT-CAAGGGCTTGAATGGGCAGGAGAAAACGGAATG GACATTGCAAACT TAAGCTTAGGTAGCTCAG CA C CTAGCGCGACACTCGAGCAAGCAGTGGATGAAG CA ACCGCAAATGGTGTCCTCGTTGTTGCCGCTT CTGGGAACTCTGGTGCAAGTTCCATT GGTTATCC AGCTCGCTATGATAATGCTATGGCCGTTGGCGCCA CCGACCAGTCAGAT GGCCTAGCTAGCTTTTCTCAG TACGGTGATGGCTTAGACATCGTTGCTCCAGGTGTT GGCATCGATAGTACCTATCCTGGTAGCTCATACGA-TAGCTTAAGTGGAACATCAATG GCAACACCTCAT GTTGCTGGTGCCGCAGCATTGGTGAAAGAAAAGA ATCCACTTTGG TCAAATGAACAAATTCGCGCTCAT-TTAAACGAAACTGCAACTGACCTTGGCGATATG TATCGTTTTGGTAATGGACTTTTAAACGCACAT GCCGCTGTTGAA.

The preproenzyme encoded by the BspAL03279.n gene is depicted in SEQ ID NO:2. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:2 sets forth the amino acid sequence of the serine protease precursor of BspAL03279 (the signal peptide sequence is underlined and in bold, the prosequence is in italics):

<u>MNRKPVKLIAGTALVMGFVISSSSISTA</u>*EETKKTYLIGFDAQEEVETFTNM*

*VDSEIGALSEEEIDITYEFKEIPVVSAEMSEEEYAALLEDPSISYIEEDIE*

*VTTMAQAIPWGISQISAPEAQIAGFTGEGVNVAVLDTGIEDHPDLNVQGGV*

SFVQGEPDYQDGNGHGTHVAGTIAALDNDEGVIGVAPNADLYAVKVLGANG

SGSVSSIAQGLEWAGENGMDIANLSLGSSAPSATLEQAVDEATANGVLVVA

ASGNSGASSIGYPARYDNAMAVGATDQSDGLASFSQYGDGLDIVAPGVGID

STYPGSSYDSLSGTSMATPHVAGAAALVKEKNPLWSNEQIRAHLNETATDL

GDMYRFGNGLLNAHAAVE.

SEQ ID NO:3 sets forth the amino acid sequence of the predicted mature protease BspAL03279 (269 amino acids): AQAIPWGISQISAPEAQIAGFTGEGVNVAVLDTGIE DHPD LNVQGGVSFVQGEPDYQDGNGHGTHVAG-TIAALDNDEGVIGVAPNADLYAVKVLGAN GSGSVS-SIAQGLEWAGENGMDIANLSLGSSAPSATLEQAVDE ATANGVLVVAASGNSG ASSIGYPARYDNAMAVGA TDQSDGLASFSQYGDGLDIVAPGVGIDSTYPGSSYD-SLSGT SMATPHVAGAAALVKEKNPLWSNEQIRAHL-NETATDLGDMYRFGNGLLNAHAAVE.

In *Bacillus* sp. DSM 8717, another gene was identified encoding a serine protease. The nucleotide sequence of this gene, BspAK01305.n, is depicted in SEQ ID NO:4:AT-GAAGA AAAGATCAAACGTTTTAATCGCAGGAAC AGCGATCGCAACCATTGCTTTAATAGGA ACACCA TCCATTTCAGAAGCTGCAGAGGAAAAAAAATCTT-ATTTAATTGGCTTTGAT GAACCTCAAGAAGTTGA GCAATTTACAACAAATTTGGAAGAAGAGATTCGTA-CACA AGCAGATGATGCTATTGATGTAACGTACGA GTTTAAAGATATTCCTGTTCTTGCCGT AGATATGAC GGAAGAAGAAATGACTGAACTCAAAAATGAAGAG AGTATTTCCTATA TTGAAGAAGATCAAGAAGTG ACAACGATGGCGCAAAGCATTCCATGGGGAATT-GAA AGAATTGGCACGCCAGCAGCACACGCATCAG-GATTCACAGGTAGCGGTGTAAGTGT CGCGGTCCTT-GATACAGGGATTGATCCACATTCTGACTTAAATGT-ACAAGGGGGGGT TAGTTTTGTACCAGGCGAAA GTG GAGCAGATGATGGAAATGGACACGGTACT-CATG TAGCAGGAACGATTGCAGCGTTAGATAATG ATGAAGGCGTTTTAGGCGTTGCTCCAG AGGTTGAT CTCTTTGCAGTAAAAGTTTTAAGTGCATCTGGATC AGGATCAATTAGTT CGATTGCGCAAGGTTTAGAG TGGACAGCTGAAAACAACATTGATGTGGCTAAT-TTA AGCTTAGGCAGTCCCTCTCCTAGTCAGACGCT AGAACAAGCGGTTAATGACGCCAC AGATAGTGG T GTGCTTGTAGTAGCAGCAGCAGGGAATTCTGGAA CAAGCTCATTAG GTTATCCAGCTCGTTATGATAAT GCAATGGCTGTTGGCGCTACCGACCAATCCGATA GCCTGGCTAGCTTCTCACAGTATGGCGAGGGTCT-TGACTTAGTCGCTCCTGGTGTTG GTGTAGAAAG-CACGTACCCAGGTGGAGGTTATGACAGCTTAAGC-GGCACATCTATG GCTGCTCCACATGTTGCAGGT-GCAGCAGCACTCGTTAAACAAAAAAATCCAGG-CTG GACAAACGAACAAATACGAAGCCATTTAAAC-GATACAGCCAATGATCTTGGCGATT CGTTCCGCT-TCGGTAGTGGCTTATTGAATGCCGAAAATGCCGTT-CAA.

The preproenzyme encoded by the BspAK01305.n gene is depicted in SEQ ID NO:5. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:5 sets forth the amino acid sequence of the serine protease precursor of BspAK01305 (the signal peptide sequence is underlined and in bold, the prosequence is in italics):

MKKRSNVLIAGTAIATIALIGTPSISEAAEEKKSYLIGFDEPQEVEQFTTN

LEEEIRTQADDAIDVTYIEFKDIPVLAVDMTEEEMTELKNEESISYIEEDQ

EVTTMAQSIPWGIERIGTPAAHASGFTGSGVSVAVLDTGIDPHSDLNVQGG

VSFVPGESGADDGNGHGTHVAGTIAALDNDEGVLGVAPEVDLFAVKVLSAS

GSGSISSIAQGLEWTAENNIDVANLSLGSPSPSQTLEQAVNDATDSGVLVV

AAAGNSGTSSLGYPARYDNAMAVGATDQSDSLASFSQYGEGLDLVAPGVGV

ESTYPGGGYDSLSGTSMAAPHVAGAAALVKQKNPGWTNEQIRSHLNDTAND

LGDSFRFGSGLLNAENAVQ.

SEQ ID NO:6 sets forth the amino acid sequence of the predicted mature protease BspAK01305 (269 amino acids): AQSIPWGIERIGTPAAHASGFTGSGVSVA-VLDTGIDPHS DLNVQGGVSFVPGESGADDGNGHGTHVAG-TIAALDNDEGVLGVAPEVDLFAVKVLSA SGSGSIS-SIAQGLEWTAENNIDVANLSLGSPSPSQTLEQAVN-DATDSGVLVVAAAGNSGT SSLGYPARYDNAMAVGATDQSDSLASFSQYGEGLD-LVAPGVGVESTYPGGGYDSLSGT SMAAPHVAGAAALVKQKNPGWTNEQIRSHLND-TANDLGDSFRFGSGLLNAENAVQ.

In *B. pseudalcaliphilus* DSM 8725, another gene was identified that encodes a serine protease. The nucleotide sequence of this gene, Bps02003.n, is depicted in SEQ ID NO:7: GTG AATCAAGGATGGAAAAAACTTCTCACA-ATGACAGCGGTTGTTTTATTATTTTCATTA ACAAGT-ATGACAGTATTGGCAGATGAAGAGAAAAAGACCT-ATTTAATCGGGTTCCA TAATCAGCTAGATGTCAA-CGAATTTATTGAGGAGGATGTAACGAATACAAA-TGGCG TGCAATTATATACGTCAGAGGATAAGTCT-GCACAGGTACAATTAGAGGTCTTACATG AATTTGA-GCAAATCCCAGTTGTTGCTGTTGAGCTGAGTCC-AGCTGATATCAAGGCAT TAGAGGCAGAGTCAGGT-ATTGCCTATATTGAAGAAGACTTTGACGTTACGAT-TGCGA ACCAAACCGTACCGTGGGGAATCGCTCA-GG- TACAAGCTCCACAAGCGCATGAATTA GGC-CACAGTGGGTCAGGAACAAAAGTAGCGGTACTT-GATACTGGTATTGCTGAGCA TGCTGATTTATTCATT-CATGGAGGAGCAAGCTTTGTTGCAGGTGAGCCAG-ATTATCA TGATTTAAATGGGCACGGAACTCACGT-AGCAGGAACAATCGCTGCACTTAATGATG GAGCC-GGAGTAATCGGTGTTGCACCAGACGCAGAATTAT-ATGCGGTCAAAGTATTA GGGGCAAGTGGT- AGTG-GTTCGGTAAGTTCAATTGCACAAGGTTTAGAAT-GGGCTGG TGATAATGGTATGGACGTAGCCAATCT-AAGCTTAGGTAGCCCGGTTGGTAGTGATAC GTTAG-AGCAAGCAGTTAATTACGCAACGGATTCAGGGG-TTCTTGTTGTGGCTGCTTC TGGTAATAGTGGG-TCAGGGACTGTTTCTTACCCAGCTCGATATGATA-ACGCATTTGC TGTTGGTGCAACAGACCAAGTGAA- TAACCGTGCAAGCTTTTCACAATATGGAACGG GGT-TAGATATTGTCGCACCTGGTGTTGAAGTTGAAAG-TACGTACTTAAATGGTGAGT ATGCGAGCTTGAG-TGGTACTTCCATGGCGACACCACATGTCGCGG-GGGTCGCGGCGT TAATAAAAGCTAAAAATCCAA-TGTTATCTAATGAAGAGATTCGTCAGCAATTAGTTC AGACAGCTACACCGTTAGGAAGTGCTGATATGTA-TGGAAGTGGTTTAGTTAATGCAG AGGTGGCTGTA-CAA.

The preproenzyme encoded by the Bps02003.n gene is depicted in SEQ ID NO:8. At the N-terminus, the protein has a signal peptide with a length of 27 amino acids as predicted by SignalP-NN (Emanuelsson et al., Nature Protocols (2007) 2: 953-971). The presence of a signal peptide indicates that this serine protease is a secreted enzyme. The enzyme has a pro sequence which is predicted to be 87 amino acids.

SEQ ID NO:8 sets forth the amino acid sequence of the serine protease precursor of Bps02003 (the signal peptide sequence is underlined and in bold, the prosequence is in italics):

VNQGWKKLLTMTAVVLLFSLTSMTVLADEEKKTYLIGFHNQLDVNEFIEED

VTNTNGVQLYTSEDKSAQVQLEVLHEFEQIPVVAVELSPADIKALEAESGI

AYIEEDFDVTIANQTVPWGIAQVQAPQAHELGHSGSGTKVAVLDTGIAEHA

DLFIHGGASFVAGEPDYHDLNGHGTHVAGTIAALNDGAGVIGVAPDAELYA

VKVLGASGSGSVSSIAQGLEWAGDNGMDVANLSLGSPVGSDTLEQAVNYAT

DSGVLVVAASGNSGSGTVSYPARYDNAFAVGATDQVNNRASFSQYGTGLDI

VAPGVEVESTYLNGEYASLSGTSMATPHVAGVAALIKAKNPMLSNEEIRQQ

LVQTATPLGSADMYGSGLVNAEVAVQ.

SEQ ID NO:9 sets forth the amino acid sequence of the predicted mature protease Bps02003 (269 amino acids): NQTVPWGIAQVQAPQAHELGHSGSGTKVAVLDTGI-AEHAD LFIHGGASFVAGEPDYHDLNGHGTHVAG-TIAALNDGAGVIGVAPDAELYAVKVLGASG SGSVS-SIAQGLEWAGDNGMDVANLSLGSPVGSDTLEQAVN-YATDSGVLVVAASGNSGS GTVSYPARYDNAFAV-GATDQVNNRASFSQYGTGLDIVAPGVEVESTYLNG-EYASLSGT SMATPHVAGVAALIKAKNPMLSNEE-IRQQLVQTATPLGSADMYGSGLVNAEVAVQ.

In *B. oshimensis* NCIMB 14023, another gene was identified encoding a serine protease. The nucleotide sequence of this gene, Bohn00569.n, is depicted in SEQ ID NO: 10:

ATGAAGAAAAGAACACACGTATTAATTGCAGGAACAGCAGTCGCAACCATT

GCTTTAATAGGAACACCATCCATTTCAGAAGCAGCAGAGGAAAAAAAATCT

TATTTAATTGGCTTTGATGAACCTCAGGAAGTGGAGCAATTTACAACAAAT

TTAGCAGAAGAGATTCGCACACAAGCAGATGATGCGATTGATGTAACGTAC

GAATTTAAGGAGATTCCTGTTCTTGCAGTAGAAATGACAGAAGAAGAGATG

GCTGAACTCAAAAATGAAGAGTATTTCCTATATTGAAGAGGATCAAGAA

```
GTGACAACGATGGCACAAAGCATTCCATGGGGAATCGAAAGAATTGGCACG

CCAGCTGCACAGGCCTCAGGATTTACAGGCAGTGGTGTAAGTGTAGCAGTC

CTTGATACAGGAATTGATCCACACTCTGACTTAAATATACAAGGTGGCGTT

AGTTTTGTACCAGGCGAAAGTGGGTCAGATGATGGAAATGGACACGGTACT

CATGTAGCAGGTACGATTGCAGCGTTAGATAATGATCAAGGGGTATTGGGT

GTTGCGCCAGACGTTGATCTTTTTGCAGTAAAAGTCTTAAGTGCTTCTGGA

TCAGGATCGATTAGTTCGATTGCGCAAGGGTTAGAGTGGACAGCAGAAAAC

AATATTGATGTAGCCAATCTAAGTTTAGGAAGCCCCTCTCCTAGTCAGACA

TTAGAGCAAGCGGTTAATGATGCCACAGATAGCGGTGTGCTTGTAGTAGCA

GCAGCAGGGAATTCTGGGACAAGTTCATTAGGATATCCAGCTCGTTATGAT

CATGCAATGGCTGTTGGCGCTACCGATGAGTCGGATAGTCTCGCTAGCTTC

TCACAGTATGGAGAGGGACTCGATTTAGTCGCACCTGGCGTTGGTGTAGAA

AGTACGTACCCAGGTGGAGGTTATGACAGCTTAAGCGGAACATCTATGGCT

GCTCCACATGTTGCAGGTGCCGCAGCACTCGTTAAGCAAAAAAATCCAAGC

TGGACAAACGAACAAATACGAGGCCATTTAAACGATACAGCCAATGATCTT

GGCGATTCGTTCCGCTTTGGTAGTGGCTTACTGAATGTTGAAAATGCCGTT

CAA.
```

The preproenzyme encoded by the Bohn00569.n gene is depicted in SEQ ID NO:11. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:11 sets forth the amino acid sequence of the serine protease precursor of Bohn00569 (the signal peptide sequence is underlined and in bold, the prosequence is in italics):

MKKRTHVLIAGTAVATIALIGTPSISEAAEEKKSYLIGFDEPQEVEQFTTN

LAEEIRTQADDAIDVLYEFKEIPVLAVEMTEEEMAELKNEESISYIEEDQE

VTTMAQSIPWGIERIGTPAAQASGFTGSGVSVAVLDTGIDPHSDLNIQGGV

SFVPGESGSDDGNGHGTHVAGTIAALDNDQGVLGVAPDVDLFAVKVLSASG

SGSISSIAQGLEWTAENNIDVANLSLGSPSPSQTLEQAVNDATDSGVLVVA

AAGNSGTSSLGYPARYDHAMAVGATDESDSLASFSQYGEGLDLVAPGVGVE

STYPGGGYDSLSGTSMAAPHVAGAAALVKQKNPSWTNEQIRGHLNDTANDL

GDSFRFGSGLLNVENAVQ.

SEQ ID NO: 12 sets forth the amino acid sequence of the predicted mature protease Bohn00569 (269 amino acids): AQSIPWGIERIGTPAAQASGFTGSGVSVAVLDTGID-PHSDLNIQGGVSFVPGESGSDDGNGHGTHVAGTIA-ALDNDQGVLGVAPDVDLFAVKVLSASGSGSISSIAQ-GLEWTAENNIDVANLSLGSPSPSQTLEQAVNDATDS-GVLVVAAAGNSGTSSL GYPARYDHAMAVGATDESD-SLASFSQYGEGLDLVAPGVGVESTYPGGGYDSLSGT-SM AAPHVAGAAALVKQKNPSWTNEQIRGHLNDTA-NDLGDSFRFGSGLLNVENAVQ.

In *B. patagoniensis* DSM 16117, another gene was identified encoding a serine protease. The nucleotide sequence of this gene, Bpan04382.n, is depicted in SEQ ID NO:13:

```
ATGAATCGAAAACCAGTTAAACTAATCGCAGGAACAGTTCTTGTTATGGGC

TTTGTCATCAGTTCATCATCCATATCAACTGCCGAGGAAACAAAAAAGACT

TATCTTATTGGTTTTGACGCTCAGGAAGAAGTCGAAACATTCACGAATATC

GTTGATTCTGAGATAGGGGCTTTATCTGAAGAAGATATTGACATTACCTAC

GAATTTAAAGACATACCGGTCGTCTCTGCTGAAATGAGTGATGAGGAGTAT

GCAGCATTACTAGAAGACCCATCGATATCATATATTGAAGAAGACATCGAA

GTAACAACAATGGCCCAAACCATTCCATGGGGCATTAGTCAAATTAGTGCT

CCTGAAGCACAAATCGCTGGATTTACTGGTGAGGGCGTAAACGTCGCGGTG

CTGGATACTGGAATAGAAGATCACCCCGACTTAAACGTTCAAGGCGGTGTT

AGCTTTGTTCAAGGAGAGCCGGATTATCAGGATGGAAATGGACACGGAACC

CATGTCGCCGGTACAATCGCTGCCCTTGATAACGACGAAGGCGTAATTGGA

GTCGCACCAAATGCAGATCTTTATGCAGTCAAAGTTCTTGGTGCAAATGGT

TCAGGCTCGGTCAGCTCAATTGCTCAAGGGCTTGAATGGGCAGGAGAAAAT

GGGATGGACATTGCAAACTAAGCCTAGGTAGCTCTGCACCTAGCGCGACA

CTCGAGCAAGCAGTGGATGAAGCAACCGCAAATGGCGTCCTCGTTGTAGCC

GCTTCTGGGAACTCGGGTGCAAGTTCTATTGGTTATCCGGCTCGCTATGAT

AACGCTATGGCCGTTGGCGCCACCGACCAGTCAGACAGCCTAGCTAACTTT

TCTCAATATGGCGAAGGCTTAGACATTGTAGCTCCAGGTGTTGGCATCGAT

AGTACCTATACTGGCAGCTCATACGACAGCTTAAGTGGAACATCAATGGCC

ACCCCTCATGTTGCTGGATCCGCAGCATTGGTGAAGAAAAGAATCCACTT

TGGTCAAATGAACAAATTCGTGCTCATTTAAACGAAACTGCAACTGACCTT

GGAGATACGTATCGTTTTGGTAATGGGCTTTTAAACGCACATGCCGCTGTT

GAA.
```

The preproenzyme encoded by the Bpan04382.n gene is depicted in SEQ ID NO:14. At the N-terminus, the protein has a signal peptide with a length of 28 amino acids as predicted by SignalP-NN. The presence of a signal peptide indicates that this serine protease is a secreted enzyme. The enzyme has a pro sequence which is predicted to be 78 amino acids.

SEQ ID NO:14 sets forth the amino acid sequence of the serine protease precursor of Bpan04382 (the signal peptide sequence is underlined and in bold, the prosequence is in italics):

MNRKPVKLIAGTVLVMGFVISSSSISTAEETKKTYLIGFDAQEEVETFTNI

VDSEIGALSEEDIDITYEFKDIPVVSAEMSDEEYAALLEDPSISYIEEDIE

VTTMAQTIPWGISQISAPEAQIAGFTGEGVNVAVLDTGIEDHPDLNVQGGV

SFVQGEPDYQDGNGHGTHVAGTIAALDNDEGVIGVAPNADLYAVKVLGANG

SGSVSSIAQGLEWAGENGMDIANLSLGSSAPSATLEQAVDEATANGVLVVA

ASGNSGASSIGYPARYDNAMAVGATDQSDSLANFSQYGEGLDIVAPGVGID

STYTGSSYDSLSGTSMATPHVAGSAALVKEKNPLWSNEQIRAHLNETATDL

GDTYRFGNGLLNAHAAVE.

SEQ ID NO:15 sets forth the amino acid sequence of the predicted mature protease Bpan04382 (269 amino acids): AQTIPWGISQISAPEAQIAGFT GEGVNVAVLDTGIE-DHPDL NVQGGVSFVQGEPDYQDGNGHGTHVAG-TIAALDNDEGVIGVAPNADLYAVKVLGANG SGSVS-SIAQGLEWAGENGMDIANLSLGSSAPSATLEQAVD-EATANGVLVVAASGNSGA SSIGYPARYDNAMAVGA-TDQSDSLANFSQYGEGLDIVAPGVGIDSTYTGSSYD-SLSGTS MATPHVAGSAALVKEKNPLWSNEQIRAHL-NETATDLGDTYRFGNGLLNAHAAVE.

Example 2

Heterologous Expression of *Bacillus* sp. Serine Proteases

BspAL03279, BspAK01305, Bps02003, Bohn00569, and Bpan04382 proteases were produced in *B. subtilis* using an expression cassette consisting of the *B. subtilis* aprE promoter, the *B. subtilis* aprE signal peptide sequence, the native protease pro-peptides, and the mature gene of interest protease and a BPN' terminator. The cassettes were cloned into the pBN based replicating shuttle vector (Babe' et al. (1998), Biotechnol. Appl. Biochem. 27: 117-124) and a suitable *B. subtilis* strain was transformed with the vectors.

A representative plasmid map of the pBN vector containing BspAL03279 gene (pBN− BspAL03279) is shown in FIG. 1. To produce BspAL03279, BspAK01305, Bps02003, Bohn00569, and Bpan04382, *B. subtilis* transformants containing pBN− BspAL03279, pBN− BspAK01305, pBN− Bps02003, pBN− Bohn00569, and pBN− Bpan04382 were cultured in 15 ml Falcon tubes for 16 hours in TSB (broth) with 10 ppm neomycin, and 300 µl of the pre-cultures were added to a 500 mL flask filled with 30 mL of cultivation media (described below) supplemented with 10 ppm neomycin. The flasks were incubated for 48 hours at 32° C. with constant rotational mixing at 180 rpm. Cultures were harvested by centrifugation at 14500 rpm for 20 min in conical tubes. The culture supernatants were used for assays. The cultivation media was an enriched semi-defined media based on MOPs buffer, with urea as major nitrogen source, glucose as the main carbon source, and supplemented with 1% soytone for robust cell growth.

The nucleotide pro-mature sequence of the BspAL03279 gene in plasmid pBN− BspAL03279 is depicted in SEQ ID NO:16: GAGGAAACAAAAAAGACTTATCTTATTG GC TTTGATGCTCAGGAAGAAGTCGAAACATTCACGA-ATATGGTCGATTCTGAGATAGG GGCTCTATCTGAA-GAAGAAATTGATATTACCTACGAATTTAAAGAA-ATACCGGTCGT CTCTGCTGAAATGAGTGAAGAA-GAATATGCAGCATTACTAGAAGACCCATCGATAT CATATATTGAAGAAGACATCGAAGTAACAACAA-TGGCCCAAGCCATTCCATGGGGA ATTAGTCAAATT-AGTGCCCCTGAAGCGCAAATTGCTGGATTTACTG-GTGAGGGTGTA AATGTTGCGGTGCTGGATACTG-GAATAGAGGATCACCCCGATTTAAACGTTCAAGGC GGTGTTAGCTTTGTTCAAGGAGAGCCGGATTATC-AGGATGGAAATGGACACGGAACCCATGTCGCCG-GTACAATCGCTGCCCTTGATAACGACGAAGGCG-TAATTGGAGTCGCACCAAATGCAGATCTTTATG-CAGTCAAAGTTCTGGGTGCAAATGGTTCTGGCTC-AGT CAGCTCAATTGCTCAAGGGCTTGAATGGGCA GAGAAAACGGAATGGACATTGCAA ACTTATCATT-AGGTAGCTCAGCACCTAGCGCGACATGGAACA-AGCAGTGGATGAA GCAACCGCAAATGGTGTCCTC-GTTGTTGCCGCTTCTGGGAACTCTGGTGCAAGT-TCC ATTGGTTATCCAGCTCGCTATGATAATGCTATG-GCCGTTGGCGCCACCGACCAGTCA GATGGCCTAG-CATCATTTTCTCAGTACGGTGATGGCTTAGACAT-CGTTGCTCCAGGT GTTGGCATCGATAGTACCTAT-CCTGGTAGCTCATACGATAGCTTAAGTGGAACATCA ATGGCAACACCTCATGTTGCTGGTGCCGCAGCAT-TGGTGAAAGAAAAGAATCCACTT TGGTCAAATGA-ACAAATTCGCGCTCATTTAAACGAAACTGCAACT-GACCTTGGCGAT ATGTATCGTTTTGGTAATGGACT-TTTAAACGCACATGCCGCTGTTGAA.

The amino acid sequence of the BspAL03279 precursor protein expressed from plasmid pBN− BspAL03279 is depicted in SEQ ID NO:17 (the predicted pro-peptide is shown underlined text):

EETKKTYLIGFDAQEEVETFTNMVDSEIGALSEEEIDITYEFKEIPVVSAE

MSEEEYAALLEDPSISYIEEDIEVTTMAQAIPWGISQISAPEAQIAGFTGE

GVNVAVLDTGIEDHPDLNVQGGVSFVQGEPDYQDGNGHGTHVAGTIAALDN

DEGVIGVAPNADLYAVKVLGANGSGSVSSIAQGLEWAGENGMDIANLSLGS

SAPSATLEQAVDEATANGVLVVAASGNSGASSIGYPARYDNAMAVGATDQS

DGLASFSQYGDGLDIVAPGVGIDSTYPGSSYDSLSGTSMATPHVAGAAALV

KEKNPLWSNEQIRAHLNETATDLGDMYRFGNGLLNAHAAVE.

The nucleotide pro-mature sequence of the BspAK01305 gene in plasmid pBN− BspAK01305 is depicted in SEQ ID NO:18: GCAGAGGAAAAAAAATCTTATTTAATTGGC TTTGATGAACCTCAAGAAGTTGAGCAATTTACAA CAAATTTGGAAGAAGAGATTCGT ACACAAGCAGA TGATGCTATTGATGTAACGTACGAGTTTAAAGATAT-TCCTGTTCTT GCCGTAGATATGACGGAAGAAGA A ATGACTGAACTCAAAAATGAAGAGAGTATTTC CTA TATTGAAGAAGATCAAGAAGTGACAACGATGG CGCAAAGCATTCCATGGGGAA TTGAAAGAATTGG CACGCCAGCAGCACACGCATCAGGATTCACAGG TAGCGGTGTA AGTGTCGCGGTCCTTGATACAGGG ATTGATCCACATTCTGACTTAAATGTTCAAGGG GG GGTTAGTTTTGTACCAGGCGAAAGTGGAGCAGAT-GATGGAAATGGACACGGTAC TCATGTAGCAGGAA CGATTGCAGCGTTAGATAATGATGAAGGCGTTTTA GGCGTTGC TCCAGAGGTTGATCTCTTTGCA GTA AAAGTTTTAAGTGCATCTGGATCAGGATCAAT TA GTTCGATTGCGCAAGGTTTAGAGTGGACAGCTGA AAACAACATTGATGTGGCTA ATTTATCTTTAGGCA GTCCCTCTCCTAGTCAGACGCTAGAACAAGCGGT-TAATGACG CCACAGATAGTGGTGTGCTTGTAGTA G CA GCAGCAGGGAACTCTGGAACAAGCTCA TTAGG TTATCCAGCTCGTTATGATAATGCAATGGCTGTTGG CGCTACCGACCAATCC GATAGCTGGCATCATTCT-CACAGTATGGCGAGGGTCTTGACTTAGTCGCTCC TGGT GTTGGTGTAGAAAGCACGTACCCAGGTGG A GGTTATGACAGCTTAAGCGGCACATC TATGGCT G CTCCACATGTTGCAGGTGCAGCAGCACTCGTTA AACAAAAAAATCCAG GCTGGACAAACGAACA A ATACGAAGCCATTTAAACGATACAGCCAATGAT CTTGGC GATTCGTTCCGCTTCGGTAGTGGCTTATT-GAATGCCGAAAATGCCGTTCAA.

The amino acid sequence of the BspAK01305 precursor protein expressed from plasmid pBN− BspAK01305 is depicted in SEQ ID NO:19 (the predicted pro-peptide is shown in underlined text):

AEEKKSYLIGFDEPQEVEQFTTNLEEEIRTQADDAIDVTYEFKDIPVLAVD

MTEEEMTELKNEESISYIEEDQEVTTMAQSIPWGIERIGTPAAHASGFTGS

GVSVAVLDTGIDPHSDLNVQGGVSFVPGESGADDGNGHGTHVAGTIAALDN

DEGVLGVAPEVDLFAVKVLSASGSGSISSIAQGLEWTAENNIDVANLSLGS

PSPSQTLEQAVNDATDSGVLVVAAAGNSGTSSLGYPARYDNAMAVGATDQS

DSLASFSQYGEGLDLVAPGVGVESTYPGGGYDSLSGTSMAAPHVAGAAALV

KQKNPGWTNEQIRSHLNDTANDLGDSFRFGSGLLNAENAVQ.

The nucleotide pro-mature sequence of the Bps02003 gene in plasmid pBN– Bps02003 is depicted in SEQ ID NO:20: GATGAAGAGAAAAAGACCTATTTAATC GG GTT CCATAATCAGCTAGATGTCAACGAATTTATTGA GGAGGATGTAACGAATACAAATG GCGTGCAATTA TATACGTCAGAGGATAAGTCTGCACAGGTACAATT-AGAGGTCTTAC ATGAATTTGAGCAAATCCCAGT TGTTGCTGTTGAGCTGAGTCCAGCTGATATCAAGG CATTAGAGGCAGAGTCAGGTATTGCCTATATTGA AGAAGACTTTGACGTTACGATTG CGAACCAAA CCGTACCGTGGGGAATCGCTCAGGTACAAGCTC-CACAAGCGCATGAA TTAGGCCACAGTGGGTCAG-GAACAAAAGTAGCGGTACTTGATACTGGTATTG CTGA GCATGCTGATTTATTCATTCATGGAGGAGCAT-CATTTGTTGCAGGTGAGCCAGATTA TCATGATTTA AATGGGCACGGAACTCACGTAGCAGGAACAATC GCTGCACTTAATG ATGGAGCCGGAGTAA TCGGT GTTGCACCAGACGCAGAATTATATGCGGTCAAA GTA TTAGGGGCAAGTGGTAGTGGTTCGGTAAGTT-CAATTGCACAAGGTTTAGAATGGGCT GGTGATA ATGGTATGGACGTAGCCAATCTATCATTAGGT AGCCCGGTTGGTAGTGAT ACGTTAGAGCAAGC AG TTAATTACGCAACGGATTCAGGGGTTCTTGTTGT GGCTGCT TCTGGTAATAGTGGGTCAGGGACTG TTTCTTACCCAGCTCGATATGATAACGCATTT GC TGTTGGTGCAACAGACCAAGTGAATAACCGTGCAT-CATTTTCACAATATGGAACG GGGTTAGATATTGT CGCACCTGGTGTTGAAGTTGAAAGTACGTACT-TAAATGGTGAG TATGCGAGCTTGAGTGGTACTTC-CATGGCGACACCACATGTCGCGGGGTCGCGGCG TTAATAAAAGCTAAAAATCCAATGTTATCTAAT-GAAGAGATTCGTCAGCAATTAGTT CAGACAGCTA CACCGTTAGGAAGTGCTGATATGTATGGAAGTG GTTTAGTTAATGCA GAGGTGGCTGTTCAA.

The amino acid sequence of the Bps02003 precursor protein expressed from plasmid pBN– Bps02003 is depicted in SEQ ID NO:21 (the predicted pro-peptide is shown in underlined text):

DEEKKTYLIGFHNQLDVNEFIEEDVTNTNGVQLYTSEDKSAQVQLEVLHEF
EQIPVVAVELSPADIKALEAESGIAYIEEDFDVTIANQTVPWGIAQVQAPQ
AHELGHSGSGTKVAVLDTGIAEHADLFIHGGASFVAGEPDYHDLNGHGTHV
AGTIAALNDGAGVIGVAPDAELYAVKVLGASGSGSVSSIAQGLEWAGDNGM
DVANLSLGSPVGSDTLEQAVNYATDSGVLVVAASGNSGSGTVSYPARYDNA
FAVGATDQVNNRASFSQYGTGLDIVAPGVEVESTYLNGEYASLSGTSMATP
HVAGVAALIKAKNPMLSNEEIRQQLVQTATPLGSADMYGSGLVNAEVAVQ.

The nucleotide pro-mature sequence of the Bohn00569 gene in plasmid pBN− Bohn00569 is depicted in SEQ ID NO:22: GCAGAGGAAAAAAAATCTTATTTAATTGGCT TTGATGAACCTCAGGAAGTGGAGCAATTTACAAC AAATTTAGCAGAAGAGATTCGC ACACAAGCAGAT-GATGCGATTGATGTAACGTACGAATTTAAGGAGAT-TCCTGTTCTT GCAGTAGAAATGACAGAAGA GAGA TGGCTGAACTCAAAAATGAAGAGAGTATTTC CTAT-ATTGAAGAGGATCAAGAAGTGACAACGATGGCAC AAAGCATTCCATGGGGAA TCGAAAGAATTGGCA GCCAGCTGCACAGGCCTCAGGATTTACAGGCAGT GGTGTA AGTGTAGCAGTCCTTGATACAGGAATT-GATCCACACTCTGACTTAAATATACAAGGT GGCGT-TAGTTTTGTACCAGGCGAAAGTGGGTCAGATGATG-GAAATGGACACGGTAC TCATGTAGCAGGTACGA TTG CAGCGTTAGATAATGATCAAGGGGTATTGGGT GTTGC GCCAGACGTTGATCTTTTTGCAGTAAAAG T CTTAAGTGCTTCTGGATCAGGATCGAT TAGTTCGA TTGCGCAAGGGTTAGAGTGGACAGCAGAAAAC AATATTGATGTAGCCA ATCTAAGTTTAGGAAGCCCC TCTCCTAGTCAGACATTAGAGCAAGCGGTTAATGA TG CCACAGATAGCGGTGTGCTTGTAGTAGCAGCA GCAGGGAACTCTGGGACAAGTTCA TTAGGATATC CAGCTCGTTATGATCATGCAATGGCTGTTGGCGC-TACCGATGAGTCG GATAGTCTCGCATCATTCTCA CAGTATGGAGAGGGACTCGATTTAGTCGCACC TGGC GTTGGTGTAGAAAGTACGTACCCAGGTGGA GGTTATGACAGCTTAAGCGGAACATC TATGGCTG CTCCACATGTTGCAGGTGCCGCAGCACTCGTTA AGCAAAAAAATCCAAG CTGGACAAACGAACA A ATACGAGGCCATTTAAACGATACAGCCAATGATC TTGGCG ATTCGTTCCGCTTTGGTAGTGGCTTACTGA ATGTTGAAAATGCCGTTCAA.

The amino acid sequence of the Bohn00569 precursor protein expressed from plasmid pBN− Bohn00569 is depicted in SEQ ID NO:23 (the predicted pro-peptide is shown in underlined text):

AEEKKSYLIGFDEPQEVEQFTTNLAEEIRTQADDAIDVTYEFKEIPVLAVE
MTEEEMAELKNEESISYIEEDQEVTTMAQSIPWGIERIGTPAAQASGFTGS
GVSVAVLDTGIDPHSDLNIQGGVSFVPGESGSDDGNGHGTHVAGTIAALDN
DQGVLGVAPDVDLFAVKVLSASGSGSISSIAQGLEWTAENNIDVANLSLGS
PSPSQTLEQAVNDATDSGVLVVAAAGNSGTSSLGYPARYDHAMAVGATDES
DSLASFSQYGEGLDLVAPGVGVESTYPGGGYDSLSGTSMAAPHVAGAAALV
KQKNPSWTNEQIRGHLNDTANDLGDSFRFGSGLLNVENAVQ.

The nucleotide pro-mature sequence of the Bpan04382 gene in plasmid pBN− Bpan04382 is depicted in SEQ ID NO:24: GAGGAAACAAAAAAGACTTATCTTATTG-GTT TTGACGCTCAGGAAGAAGTCGAAACATTCA-CGAATATCGTTGATTCTGAGATAGGG GCTTTATCT-GAAGAAGATATTGACATTACCTACGAATTTAAAGA-CATACCGGTCGTC TCTGCTGAAATGAGTGATGAG-GAGTATGCAGCATTACTAGAAGACCCATCGATATC ATATATTGAAGAAGACATCGAAGTAACAACAA-TGGCCCAAACCATTCCATGGGGCA TTAGTCAAATT-AGTGCTCCTGAAGCACAAATCGCTGGATTTAC-TGGTGAGGGCGTAA ACGTCGCGGTGCTGGATAC-TGGAATAGAAGATCACCCCGACTTAAACGTTCAA-GGC GGTGTTAGCTTTGTTCAAGGAGAGCCGGAT-TATCAGGATGGAAATGGACACGGAAC CCATGTCG-CCGGTACAATCGCTGCCCTTGATAACGACG- AAG-GCGTAATTGGAGTCGC ACCAAATGCAGATCTT-TATGCAGTCAAAGTTCTTGGTGCAAATGGTTCAGG-CTCGGT CAGCTCAATTGCTCAAGGGCTTGAAT-GGGCAGGAGAAAATGGGATGGACATTGCAA ACT- TAAGCCTAGGTAGCTCTGCACCTAGCGCGACACTG-
GAACAAGCAGTGGATGAA GCAACCGCAAATGG-
CGTCCTCGTTGTAGCCGCTTCTGGGAACTCGGG-
TGCAAGTTCT ATTGGTTATCCGGCTCGCTATGATAA-
CGCTATGGCCGTTGGCGCCACCGACCAGTCAGAC-
AGCCTAGCTAACTTTTCTCAATATGGCGAAGGCT-
TAGACATTGTAGCTCCAGGTGTTGGCATCGATAG-
TACCTATACTGGCAGCTCATACGACAGCTTAAGTG-
GAACATCA ATGGCCACCCCTCATGTTGC- TGGCTC-
AGCAGCATTGGTGAAAGAAAAGAATCCACTTTG-
GTCAAATGAACAAATTCGTGCTCATTTAAACGAA-
ACTGCAACTGACCTTGGAGATACGTATCGTTTT-
GGTAATGGGCTTTTAAACGCACATGCCGCTGTT-
GAATAA.

The amino acid sequence of the Bpan04382 precursor protein expressed from plasmid pBN– Bpan04382 is depicted in SEQ ID NO:25 (the predicted pro-peptide is shown in underlined text):

EETKKTYLIGFDAQEEVETFTNIVDSEIGALSEEDIDITYEFKDIPVVSAE

MSDEEYAALLEDPSISYIEEDIEVTTMAQTIPWGISQISAPEAQIAGFTGE

GVNVAVLDTGIEDHPDLNVQGGVSFVQGEPDYQDGNGHGTHVAGTIAALDN

DEGVIGVAPNADLYAVKVLGANGSGSVSSIAQGLEWAGENGMDIANLSLGS

SAPSATLEQAVDEATANGVLVVAASGNSGASSIGYPARYDNAMAVGATDQS

DSLANFSQYGEGLDIVAPGVGIDSTYTGSSYDSLSGTSMATPHVAGSAALV

KEKNPLWSNEQIRAHLNETATDLGDTY.

N and C-Term Analysis

Bsp02003: The N-terminal is determined as N[1] by the "Protein N-terminal Acetylation" method. The C-terminal Q[269] is determined by the "isO-labelling" method Bohn00569: The N-terminal is determined as A[1] by the "Protein N-terminal Acetylation" method. The C-terminal Q[269] is determined by the "isO-labelling" method.

Protein Determination by Stain Free Imager Criterion

Protein was quantified by the stain-free Imager Criterion method. The method utilizes stain-free precast PAGE gels, where the intensity of each band will depend on amount of tryptophan residues present in the protein of interest. The Criterion™ TGX (Tris-Glycine extended) Stain-Free™ precast gels for PAGE include unique trihalo compounds. This allows rapid fluorescent detection of proteins with the Gel Doc™ EZ imaging system. The trihalo compounds react with tryptophan residues in a UV-induced reaction to produce fluorescence, which can be easily detected by the Gel Doc EZ imager within gels. Reagents used in the assay: Concentrated (10×) Laemmli Sample Buffer (Kem-En-Tec, Catalogue #42556); either 18 or 26-well Criterion TGX Strain-Free Precast gels (Bio-Rad, Catalogue #567-8124 and 567-8125, respectively); and protein markers "Precision Plus Protein Standards" (Bio-Rad, Catalogue #161-0363). The assay was carried out as follow: 25 µl protein sample and 25 µl 0.5M HCL was added to a 96-well-PCR plate on ice for 10 min to inactivate the protease and prevent self-hydrolysis. 50 µl of the acid protein mix was added to 50 µL sample buffer containing 0.385 mg DTT in the 96-well PCR plate. After that, the chamber was filled by running buffer, gel cassette was set. Then, 10 µL of each sample together with markers was loaded in each pocket and electrophoresis was started at 200 V for 35 min. Following electrophoresis, the gel was transferred to Imager. Image Lab software was used to calculate the intensity of each band. By knowing the protein amount and the tryptophan content of the standard sample, the calibration curve can be made. The amount of experimental sample can be determined by extrapolation of the band intensity and tryptophan numbers to protein concentration. The protein quantification method was employed to prepare samples of the BspAL03279, BspAK01305, Bps02003, Bohn00569, and Bpan04382 proteases used for assays shown in subsequent Examples.

N and C terminal amino acid determination of Bps02003 and Bohn00569

In preparation for sequence confirmation, a sample of isolated protein is subjected to a series of chemical treatments in a 10 kDa spinfilter. The sample is denatured and reduced by urea and DTT treatment. A guanidination step was performed to convert lysines to homoarginines to protect lysine side chains from acetylation. Acetylation reaction using iodoacetamide then modifies only the proteins' N-terminal residue. The sample is then mixed with a buffer containing $^{18}O$ water and the enzymes trypsin and chymotrypsin are added for digestion. The resulting peptides will contain mixtures of $^{18}O$ and $^{16}O$, except for the Carboxyl terminus which will retain the native $^{16}O$. The digestion products were separated and analyzed using a Proxeon nano-LC system followed by LTQ Orbitrap (Thermo Fisher) high resolution mass spectrometer and the amino acid sequence was deduced from the MS/MS fragment spectrum of the peptides, and the isotopic pattern of the peptides. A sample of Bps02003 protein expressed from plasmid pBN–Bps02003 was analyzed as described above. The sequence of the mature protein was determined to correspond to sequence listed in SEQ ID NO: 9, consisting of 269 amino acids. A sample of Bohn00569 protein expressed from plasmid pBN– Bohn00569 was analyzed as described above. The sequence of the mature protein was determined to correspond to sequence listed in SEQ ID:12, consisting of 269 amino acids.

Example 3

Protease Activity of *Bacillus* sp. Serine Proteases

The protease activities of BspAL03279, BspAK01305, Bps02003, Bohn00569, and Bpan04382 proteases were tested by measuring the hydrolysis of dimethyl casein (DMC) substrate. The reagent solutions used for the DMC assay were: 2.5% DMC (Sigma) in 100 mM Sodium Carbonate pH 9.5, 0.075% TNBSA (2,4,6-trinitrobenzene sulfonic acid, Thermo Scientific) in Reagent A. Reagent A: 45.4 g $Na_2B_4O_7 \cdot 10H_2O$ (Merck) in 15 mL 4N NaOH to reach a final volume of 1000 mL in MQ water. Dilution Solution: 10 mM NaCl, 0.1 mM $CaCl_2$, 0.005% Tween-80. Protease supernatants were diluted in Dilution Solution to appropriate concentration for the assay. A 96-well microtiter plate (MTP) was filled with 95 µl DMC substrate followed by the addition of 5 µl diluted protease supernatant. 100 µL of TNBSA in Reagent A was then added with slow mixing. Activity was measured at 405 nm over 5 min using a SpectraMax plate reader in kinetic mode at RT. The absorbance of a blank containing no protease was subtracted from the values. The activity was expressed as mOD/min. The protease activity measured for BspAL03279, BspAK01305, Bps02003, Bohn00569, and Bpan04382, proteases are shown in Table 1.

TABLE 1

Protease activity of *Bacillus* sp. serine proteases on DMC substrate

| Host Organism | Protease | Activity in DMC assay mOD/min/ppm |
|---|---|---|
| *Bacillus* sp. DSM 8714 | BspAL03279 | 84 |
| *Bacillus* sp. DSM 8717 | BspAK01305 | 75 |
| *B. pseudalcaliphilus* DSM 8725 | Bps02003 | 81 |
| *B. oshimensis* NCIMB 14023 | Bohn00569 | 97 |
| *B. patagoniensis* DSM 16117 | Bpan04382 | 60 |
| *B. lentus* | GG36 | 54 |
| *B. amyloliquifaciens* | BPN' | 23 |

The pH dependence of proteolytic activity of *Bacillus* sp. serine proteases was studied using N-suc-AAPF-pNA (AAPF) as substrate in a 50 mM Acetate/Bis-Tris/HEPES/CHES buffer. The activity was measured at pH between 4 to 11 with 1 pH unit increments. For the AAPF assay, the reagent solutions used were: 50 mM Acetate/Bis-Tris/HEPES/CHES buffer and 160 mM suc-AAPF-pNA in DMSO (suc-AAPF-pNA stock solution) (Sigma: S-7388). To prepare a working solution, 1 mL suc-AAPF-pNA stock solution was added to 100 mL Acetate/Bis-Tris/HEPES/CHES buffer and mixed. An enzyme sample was added to a MTP (Costar 9017) containing suc-AAPF-pNA working solution and assayed for activity at 405 nm over 3 min using a SpectraMax plate reader in kinetic mode at 40° C. The protease activity was expressed as mOD*min-1. The activity was converted to percentages of relative activity, by defining the activity at the optimal pH as 100%. Ranges for which the *Bacillus* sp. serine proteases maintain ≥50% of activity, under the conditions of this assay are shown in table 2.

TABLE 2 pH profile of *Bacillus* sp. serine proteases

| Host Organism | Protease | pH range for which ≥50% activity is maintained |
|---|---|---|
| *Bacillus* sp. DSM 8714 | BspAL03279 | 8-11 |
| *Bacillus* sp. DSM 8717 | BspAK01305 | 8-11 |
| *B. pseudalcaliphilus* DSM 8725 | Bps02003 | 8-11 |
| *B. oshimensis* NCIMB 14023 | Bohn00569 | 8-11 |
| *B. patagoniensis* DSM 16117 | Bpan04382 | 7-11 |
| *B. lentus* | GG36 | 8-11 |
| *B. amyloliquifaciens* | BPN'Y217L | 8-11 |

Example 4

Comparison of *Bacillus* sp. Serine Proteases to Related Molecules

Related proteins were identified by a BLAST search (Altschul et al., Nucleic Acids Res, 25:3389-402, 1997) against the NCBI non-redundant protein database using the amino acid sequences of BspAL03279 (SEQ ID NO:3), BspAK01305 (SEQ ID NO:6), Bps2003 (SEQ ID NO:9), Bohn00569 (SEQ ID NO:12), and Bpan04382 (SEQ ID NO:15) as query sequence and a subset are shown on Tables 2A-6A.

A similar search was run against the Genome Quest Patent database with search parameters set to default values using the amino acid sequences for BspAL23279 (SEQ ID NO: 3), BspAK01305 (SEQ ID NO:6), Bps02003 (SEQ ID NO:9), Bohn00569 (SEQ ID NO: 12), and Bpan04382 (SEQ ID NO:15), as the query sequence, and a subset are shown in Tables 2B-6B.

Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 2A

List of sequences with percent identity to BspAL03279 protein identified from the NCBI non-redundant protein database

| Accession # | PID | Organism | Sequence Length | Alignment Length |
|---|---|---|---|---|
| ADK62564.1 | 78 | *Bacillus* sp. B001 | 375 | 269 |
| WP_035392836 | 77 | *Bacillus* sp. JCM 19047 | 375 | 269 |
| AAA22212.1 | 76 | *Bacillus alkalophilus* | 380 | 269 |
| WP_038476582 | 76 | *Bacillus lehensis* G1 | 375 | 269 |
| BAA02442.1 | 75 | *Bacillus* sp. | 380 | 267 |
| P29600 | 75 | *Bacillus lentus* | 269 | 267 |
| BAD63300.1 | 75 | *Bacillus clausii* KSM-K16 | 380 | 267 |
| WP_042417589 | 73 | *Geomicrobium* sp. JCM 19038 | 380 | 269 |
| WP_042358689 | 73 | *Geomicrobium* sp. JCM 19055 | 380 | 269 |
| BAA25184.1 | 72 | *Bacillus* sp. AprN | 379 | 266 |
| AFK08970.1 | 72 | *Bacillus lehensis* | 378 | 266 |
| BAA06157.1 | 71 | *Bacillus* sp. Sendai | 382 | 266 |
| AAA87324.1 | 71 | *Bacillus subtilis* | 378 | 268 |
| WP_010192403.1 | 59 | *Bacillus* sp. m3-13 | 381 | 275 |
| ABI26631.1 | 58 | *Bacillus clausii* | 361 | 269 |
| BAA05540.1 | 58 | *Bacillus* sp. AprM | 361 | 269 |
| CAJ70731.1 | 57 | *Bacillus licheniformis* | 379 | 274 |
| AAT75303.1 | 57 | *Bacillus mojavensis* | 379 | 274 |

TABLE 2B

List of sequences with percent identity to BspAL03279 protein identified from the Genome Quest database

| Patent ID # | PID | Organism | Sequence Length | Alignment Length |
|---|---|---|---|---|
| EP1160327 | 76.4 | *Bacillus* sp Synthetic | 269 | 267 |
| U.S. Pat. No. 6,271,012 | 76.03 | *Bacillus* sp; PB92 Synthetic | 269 | 267 |
| WO9402618 | 76.03 | *Bacillus novalis* | 269 | 267 |
| EP0405901 | 76.03 | *Bacillus subtilis*; 309 | 269 | 267 |
| JP2012524542-0031 | 76.03 | *Bacillus clausii* | 269 | 267 |
| JP2012524542-0047 | 76.03 | *Bacillus alcalophilus* | 269 | 267 |
| US7445912-0016 | 76.03 | *Bacillus subtilis* | 269 | 267 |
| WO9402618 | 75.66 | *Bacillus novalis* | 269 | 267 |

TABLE 3A

List of sequences with percent identity to BspAK01305 protein identified from the NCBI non-redundant protein database

| Accession # | PID | Organism | Sequence Length | Alignment Length |
|---|---|---|---|---|
| WP_035392836 | 100 | *Bacillus* sp. JCM 19047 | 375 | 269 |
| ADK62564.1 | 99 | *Bacillus* sp. B001 | 375 | 269 |
| WP_038476582 | 96 | *Bacillus lehensis* G1 | 375 | 269 |
| WP_042358689 | 75 | *Geomicrobium* sp. JCM 19055 | 380 | 267 |
| WP_042417589 | 75 | *Geomicrobium* sp. JCM 19038 | 380 | 269 |
| WP_042398727 | 73 | *Geomicrobium* sp. JCM 19037 | 380 | 269 |
| AAA22212.1 | 72 | *Bacillus alkalophilus* | 380 | 269 |
| P29600 | 72 | *Bacillus lentus* | 269 | 269 |

TABLE 3A-continued

List of sequences with percent identity to BspAK01305 protein identified from the NCBI non-redundant protein database

| Accession # | PID | Organism | Sequence Length | Alignment Length |
|---|---|---|---|---|
| BAD63300.1 | 72 | Bacillus clausii KSM-K16 | 380 | 269 |
| WP_034632645 | 72 | Bacillus okhensis | 382 | 268 |
| BAA06157.1 | 70 | Bacillus sp. Sendai | 382 | 268 |
| BAA25184.1 | 69 | Bacillus sp. AprN | 379 | 268 |
| AFK08970.1 | 68 | Bacillus lehensis | 378 | 268 |
| AAA87324.1 | 68 | Bacillus subtilis | 378 | 268 |
| AGS78407.1 | 66 | Bacillus gibsonii | 375 | 268 |
| WP_010192403.1 | 60 | Bacillus sp. m3-13 | 381 | 275 |
| AAC43580.1 | 59 | Bacillus sp. SprC | 378 | 275 |

TABLE 3B

List of sequences with percent identity to BspAK01305 protein identified from the Genome Quest database

| Patent ID # | PID | Organism | Sequence Length | Alignment Length |
|---|---|---|---|---|
| U.S. Pat. No. 5,677,272 | 73.2 | Synthetic Bacillus lentus | 269 | 269 |
| WO2015044206-0010 | 73.2 | B. lentus; DSM 5483 Synthetic | 269 | 269 |
| EP1160327 | 72.9 | Bacillus sp Synthetic | 269 | 269 |
| US8389262-0001 | 72.5 | Bacillus lentus | 269 | 269 |
| US20130217607-0001 | 72.5 | Bacillus Alkalophilus PB92 | 269 | 269 |
| WO2008010925 | 72.5 | Bacillus sp.; PB92 | 380 | 269 |
| JP2012524542-0059 | 72.5 | Bacillus clausii | 382 | 269 |

TABLE 4A

List of sequences with percent identity to Bps02003 protein identified from the NCBI non-redundant protein database

| Accession # | PID | Organism | Sequence Length | Alignment Length |
|---|---|---|---|---|
| WP_047989534 | 100 | Bacillus pseudalcaliphilus | 373 | 269 |
| AAA22212.1 | 76 | Bacillus alkalophilus | 380 | 269 |
| BAD63300.1 | 76 | Bacillus clausii KSM-K16 | 380 | 268 |
| P29600 | 75 | Bacillus lentus | 269 | 268 |
| WP_047986748 | 74 | Bacillus pseudalcaliphilus | 382 | 269 |
| WP_034632645 | 74 | Bacillus okhensis | 382 | 269 |
| BAA06157.1 | 73 | Bacillus sp. Sendai | 382 | 269 |
| BAA25184.1 | 70 | Bacillus sp. AprN | 379 | 268 |
| AFK08970.1 | 70 | Bacillus lehensis | 378 | 268 |
| AAA87324.1 | 71 | Bacillus subtilis | 378 | 268 |
| AGS78407.1 | 67 | Bacillus gibsonii | 375 | 268 |
| ADK62564.1 | 67 | Bacillus sp. B001 | 375 | 268 |
| BAA02442.1 | 61 | Bacillus sp. | 361 | 269 |
| BAA05540.1 | 61 | Bacillus sp. AprM | 361 | 269 |
| ADC49870.1 | 60 | Bacillus pseudofirmus OF4 | 374 | 272 |
| ABI26631.1 | 60 | Bacillus clausii | 361 | 269 |
| WP_010192403.1 | 60 | Bacillus sp. m3-13 | 381 | 274 |

TABLE 4B

List of sequences with percent identity to Bps02003 protein identified from the Genome Quest database

| Patent ID # | PID | Organism | Sequence Length | Alignment Length |
|---|---|---|---|---|
| EP1160327 | 76.5 | Bacillus sp Synthetic | 269 | 268 |
| DE4224125 | 76.5 | Bacillus alcalophilus; HA1 DSM 5466 | 380 | 268 |
| WO03054185 | 76.1 | Bacillus alkalophilus | 268 | 268 |
| WO9402618 | 76.1 | Bacillus novalis | 269 | 268 |
| EP0415296 | 76.1 | Bacillus alcalophilus | 269 | 268 |
| US8530218-0013 | 76.1 | Bacillus clausii | 269 | 268 |
| US8530218-0047 | 76.1 | Bacillus alcalophilus | 269 | 268 |
| WO2013188344-0003 | 76.1 | Bacillus clausii | 269 | 268 |
| EP2660309-0001 | 76.1 | Bacillus alcalophilus | 269 | 268 |
| US20130171717-0006 | 76.1 | Bacillus lentus | 269 | 268 |
| JP1993361428-0006 | 76.1 | Bacillus clausii KSM-K16 | 269 | 268 |
| JP2013153763-0002 | 76.1 | B. lentus (subtilisin 309) | 273 | 268 |
| DE4224125 | 76.1 | Bacillus alcalophilus; HA1 DSM 5466 | 380 | 268 |
| WO2005118793 | 76.1 | Bacillus sp.; DSM 14390 | 380 | 268 |

TABLE 5A

List of sequences with percent identity to Bohn00569 protein identified from the NCBI non-redundant protein database

| Accession # | PID | Organism | Sequence Length | Alignment Length |
|---|---|---|---|---|
| WP_038476582 | 100 | Bacillus lehensis G1 | 375 | 269 |
| WP_035392836 | 96 | Bacillus sp. JCM 19047 | 375 | 269 |
| ADK62564.1 | 96 | Bacillus sp. B001 | 375 | 269 |
| WP_042358689 | 75 | Geomicrobium sp. JCM 19055 | 380 | 267 |
| WP_042417589 | 75 | Geomicrobium sp. JCM 19038 | 380 | 269 |
| WP_042398727 | 72 | Geomicrobium sp. JCM 19037 | 380 | 269 |
| AAA22212.1 | 71 | Bacillus alkalophilus | 380 | 269 |
| P29600 | 71 | Bacillus lentus | 269 | 269 |
| BAD63300.1 | 71 | Bacillus clausii KSM-K16 | 380 | 269 |
| BAA25184.1 | 69 | Bacillus sp. AprN | 379 | 268 |
| BAA06157.1 | 69 | Bacillus sp. Sendai | 382 | 268 |
| AFK08970.1 | 68 | Bacillus lehensis | 378 | 268 |
| AAA87324.1 | 68 | Bacillus subtilis | 378 | 268 |
| AGS78407.1 | 65 | Bacillus gibsonii | 375 | 268 |
| WP_010192403.1 | 60 | Bacillus sp. m3-13 | 381 | 275 |
| AAC43580.1 | 59 | Bacillus sp. SprC | 378 | 275 |
| WP_022628745.1 | 57 | Bacillus marmarensi | 374 | 273 |
| YP_003972439.1 | 57 | Bacillus atrophaeus 1942 | 382 | 275 |

TABLE 5B

List of sequences with percent identity to Bohn00569 protein identified from the Genome Quest database

| Patent ID # | PID | Organism | Sequence Length | Alignment Length |
|---|---|---|---|---|
| WO2015044206-0010 | 72.5 | Bacillus lentus; DSM 5483 Synthetic | 269 | 269 |
| WO9211348 | 72.5 | Bacillus subtilis Synthetic | 269 | 269 |
| U.S. Pat. No. 6,312,936 | 72.5 | Bacillus lentus Synthetic | 269 | 269 |
| DE4224125 | 72.1 | Bacillus alcalophilus; HA1 DSM 5466 | 380 | 269 |
| WO9402618 | 71.8 | Bacillus novalis | 269 | 269 |
| US20130217607-0001 | 71.8 | Bacillus Alkalophilus PB92 | 269 | 269 |
| US8530218-0013 | 71.8 | Bacillus clausii | 269 | 269 |
| US7445912-0016 | 71.8 | Bacillus subtilis | 269 | 269 |

TABLE 6A

List of sequences with percent identity to Bpan04382 protein identified from the NCBI non-redundant protein database

| Accession # | PID | Organism | Sequence Length | Alignment Length |
|---|---|---|---|---|
| ADK62564.1 | 78 | Bacillus sp. B001 | 375 | 269 |
| WP_035392836 | 77 | Bacillus sp. JCM 19047 | 375 | 269 |
| WP_038476582 | 75 | Bacillus lehensis G1 | 375 | 269 |
| AAA22212.1 | 75 | Bacillus alkalophilus | 380 | 267 |
| BAA02442.1 | 74 | Bacillus sp. | 380 | 267 |
| P29600 | 74 | Bacillus lentus | 269 | 267 |
| BAD63300.1 | 74 | Bacillus clausii KSM-K16 | 380 | 267 |
| WP_042358689 | 73 | Geomicrobium sp. JCM 19055 | 380 | 269 |
| WP_042417589 | 73 | Geomicrobium sp. JCM 19038 | 380 | 269 |
| BAA25184.1 | 72 | Bacillus sp. AprN | 379 | 266 |
| AFK08970.1 | 72 | Bacillus lehensis | 378 | 266 |
| AAA87324.1 | 71 | Bacillus subtilis | 378 | 268 |
| BAA06157.1 | 71 | Bacillus sp. Sendai | 382 | 266 |
| AGS78407.1 | 67 | Bacillus gibsonii | 375 | 266 |
| ABI26631.1 | 59 | Bacillus clausii | 361 | 269 |
| BAA02443.2 | 59 | Bacillus halodurans | 361 | 269 |
| BAA05540.1 | 59 | Bacillus sp. AprM | 361 | 269 |
| ADD64465.1 | 58 | Bacillus sp. JB99 | 361 | 269 |
| WP_010192403.1 | 58 | Bacillus sp. m3-13 | 381 | 275 |
| ADC49870.1 | 58 | Bacillus pseudofirmus OF4 | 374 | 273 |
| AAC43580.1 | 57 | Bacillus sp. SprC | 378 | 275 |
| BAD11988.2 | 57 | Bacillus sp. KSM-LD1 | 376 | 275 |
| CAJ70731.1 | 56 | Bacillus licheniformis | 379 | 274 |
| AAT75303.1 | 56 | Bacillus mojavensis | 379 | 274 |
| CAA24990.1 | 54 | Bacillus amyloliquefaciens | 376 | 275 |

TABLE 6B

List of sequences with percent identity to Bpan04382 protein identified from the Genome Quest database

| Patent ID # | PID | Organism | Sequence Length | Alignment Length |
|---|---|---|---|---|
| EP1160327 | 75.7 | Bacillus sp Synthetic | 269 | 267 |
| U.S. Pat. No. 6,271,012 | 75.3 | Bacillus sp; PB92 Synthetic | 269 | 267 |
| WO9402618 | 75.3 | Bacillus novalis | 269 | 267 |
| EP0405901 | 75.3 | Bacillus subtilis; 309 | 269 | 267 |
| WO2013188344-0003 | 75.3 | Bacillus clausii | 269 | 267 |
| US20130217607-0001 | 75.3 | Bacillus Alkalophilus PB92 | 269 | 267 |
| WO9402618 | 75.3 | Bacillus novalis | 269 | 267 |
| DE4224125 | 75.3 | Bacillus alcalophilus; HA1 DSM 5466 | 380 | 267 |
| DE19530816 | 74.9 | Bacillus lentus; DSM 5483 | 269 | 267 |

Alignment of Homologous Sequences

An alignment of the mature protein amino acid sequences for BspAL03279 (SEQ ID NO:3), BspAK01305 (SEQ ID NO:6), Bps02003 (SEQ ID NO:9), Bohn00569 (SEQ ID NO:12), and Bpan04382 (SEQ ID NO:15) with the sequences of the mature forms of various subtilisins from Tables 2A-6A is shown in FIG. 2. The sequences were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). A phylogenetic tree for amino acid sequences of the mature forms of the subtilisins from FIG. 2 was built using the Geneious Tree builder program and is displayed in FIG. 3.

Example 5

Unique Features of the BspAL03279-Clade of Subtilisins

The FIG. 2 alignment was reviewed for unique sequence similarities across the BspAL03279-clade of subtilisins. The BspAL03279-clade of subtilisins is characterized by a common motif over the sequence that begins with Aspartic acid (D250) and ends at position 269, according to BspAL03279 numbering. This motif can be characterized as DLGDXXRFGX$_a$GLLXXXXAVX (SEQ ID NO:26), where X is any amino acid and X$_a$ is N or S. FIG. 2 includes box around the motif.

Figure 3:
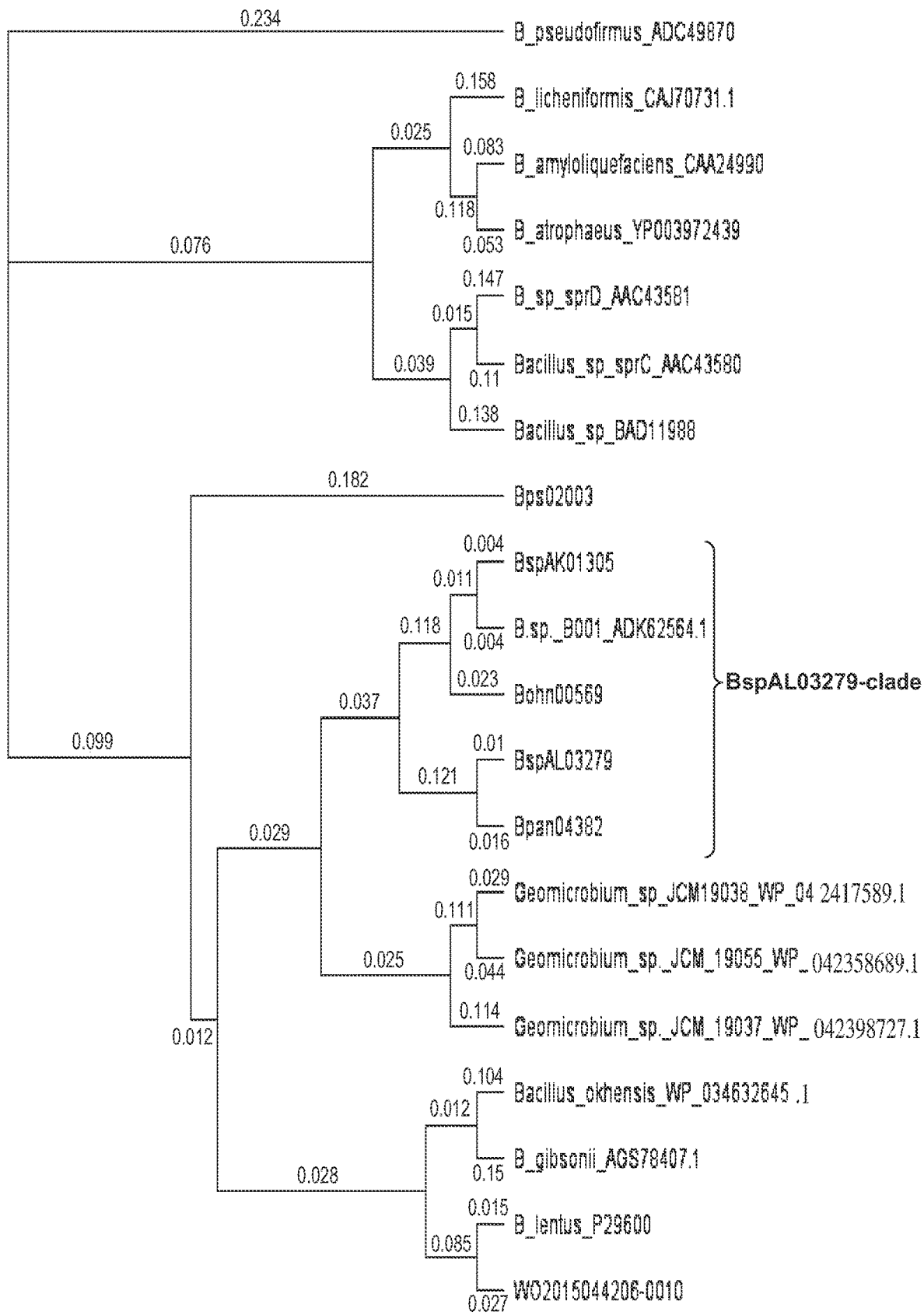
FIG. 3 provides a phylogenetic tree of subtilisins including BspAL03279, BspAK01305, Bps02003, Bohn00569, and Bpan04382.

The BspAL03279, BspAK01305, Bpan04382, Bohn00569, and ADK62564.1 subtilisins, which have been identified as a BspAL03279-clade of subtilisins based on the shared sequence motif set forth above, also cluster together in the phylogenetic tree that was built using various bacterial subtilisins and which is set forth in FIG. 3.

The amino acid identity across the mature forms of various subtilisins from Tables 2A-6A is shown on Table 7 below, wherein the percent amino acid identity is calculated over, for example, the 269 residues of the BspAL03279 mature sequence.

TABLE 7

Percent amino acid sequence identity

| Mature enzyme | 1 | 2 | 3 | 4 | 5 | 6 | 7 | 8 | 9 | 10 | 11 | 12 | 13 |
|---|---|---|---|---|---|---|---|---|---|---|---|---|---|
| 1. BspAK01305 |  | 77.3 | 77 | 96.3 | 67.7 | 99.3 | 74.7 | 74.7 | 72.9 | 72.1 | 65.8 | 72.5 | 73.2 |
| 2. BspAL03279 | 77.3 |  | 97.4 | 75.8 | 69.5 | 78.1 | 73.2 | 72.9 | 69.5 | 70.6 | 66.5 | 75.1 | 75.1 |
| 3. Bpan04382 | 77 | 97.4 |  | 75.5 | 69.5 | 77.7 | 72.9 | 72.9 | 69.1 | 70.3 | 66.5 | 74.3 | 74.3 |
| 4. Bohn00569 | 96.3 | 75.8 | 75.5 |  | 66.9 | 96.3 | 74.7 | 74.3 | 72.1 | 71 | 65.1 | 71.7 | 72.5 |
| 5. Bps02003 | 67.7 | 69.5 | 69.5 | 66.9 |  | 67.7 | 66.5 | 67.7 | 67.7 | 73.6 | 67.7 | 75.8 | 72.1 |
| 6. ADK62564.1 | 99.3 | 78.1 | 77.7 | 96.3 | 67.7 |  | 75.1 | 75.1 | 72.5 | 71.7 | 65.8 | 72.5 | 73.2 |
| 7. WP_042417589.1 | 74.7 | 73.2 | 72.9 | 74.7 | 66.5 | 75.1 |  | 92.9 | 78.4 | 69.9 | 66.9 | 74.3 | 76.6 |
| 8. WP_042358689.1 | 74.7 | 72.9 | 72.9 | 74.3 | 67.7 | 75.1 | 92.9 |  | 75.8 | 69.9 | 66.2 | 74.3 | 75.1 |
| 9. WP_042398727.1 | 72.9 | 69.5 | 69.1 | 72.1 | 67.7 | 72.5 | 78.4 | 75.8 |  | 76.6 | 71 | 75.8 | 75.8 |
| 10. WP_034632645.1 | 72.1 | 70.6 | 70.3 | 71 | 73.6 | 71.7 | 69.9 | 69.9 | 76.6 |  | 77.7 | 82.2 | 79.9 |
| 11. AGS78407.1 | 65.8 | 66.5 | 66.5 | 65.1 | 67.7 | 65.8 | 66.9 | 66.2 | 71 | 77.7 |  | 79.9 | 77.7 |
| 12. P29600 | 72.5 | 75.1 | 74.3 | 71.7 | 75.8 | 72.5 | 74.3 | 74.3 | 75.8 | 82.2 | 79.9 |  | 95.9 |
| WO2015044206-0010 | 73.2 | 75.1 | 74.3 | 72.5 | 72.1 | 73.2 | 76.6 | 75.1 | 75.8 | 79.9 | 77.7 | 95.9 |  |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

We claim:

1. A method of cleaning comprising contacting a surface or an item in need of cleaning with a composition comprising a surfactant and a subtilisin comprising a DLGDXXRFGXaGLLXXXXAVX (SEQ ID NO:26) motif, wherein X is any amino acid and Xa is N or S, wherein said subtilisin comprises an amino acid sequence having at least 85% amino acid sequence identity to the amino acid sequence of SEQ ID NO: 3, wherein the subtilisin has improved protease activity when compared to protease activity of *Bacillus lentus* GG36 subtilisin; and optionally further comprising the step of rinsing said surface or item after contacting said surface or item with said composition.

2. The method of claim 1, wherein said item is dishware or fabric.

3. A method for producing a subtilisin comprising:
(a) stably transforming a host cell with an expression vector encoding a subtilisin comprising a DLGDXXRFGXaGLLXXXXAVX (SEQ ID NO:26) motif, wherein X is any amino acid and Xa is N or S, wherein said subtilisin comprises an amino acid sequence having at least 85% amino acid sequence identity to the amino acid sequence of SEQ ID NO: 3, wherein the subtilisin has improved protease activity when compared to protease activity of *Bacillus lentus* GG36 subtilisin;
(b) cultivating said transformed host cell under conditions suitable for said host cell to produce said subtilisin polypeptide; and
(c) recovering said subtilisin or polypeptide.

4. The method of claim 3, wherein said expression vector comprises a heterologous polynucleotide sequence encoding a heterologous pro-peptide.

5. The method of claim 3, wherein said expression vector comprises one or both of a heterologous promoter and a polynucleotide sequence encoding a heterologous signal peptide.

6. The method of claim 1, wherein the surfactant is selected from the group consisting of an anionic surfactant, a cationic surfactant, a zwitterionic surfactant, an ampholytic surfactant, a semi-polar non-ionic surfactant, and a combination thereof.

7. The method of claim 1, wherein the composition is a detergent composition.

8. The method of claim 7, wherein the detergent composition is selected from the group consisting of a laundry detergent, a fabric softening detergent, a dishwashing detergent, and a hard-surface cleaning detergent.

9. The method of claim 1, wherein the composition further comprises at least one calcium ion and/or zinc ion; at least one stabilizer; from about 0.001% to about 1.0 weight % of said subtilisin or recombinant polypeptide; at least one bleaching agent; at least one adjunct ingredient; and/or one or more additional enzymes or enzyme derivatives selected from the group consisting of acyl transferases, alpha-amylases, betaamylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

10. The method of claim 1, wherein the composition is a granular, powder, solid, bar, liquid, tablet, gel, paste or unit dose composition.

11. The method of claim 1, wherein the composition is formulated at a pH of from about 8 to about 12.

\* \* \* \* \*

SEQUENCE LISTING

```
Sequence total quantity: 46
SEQ ID NO: 1              moltype = DNA  length = 1125
FEATURE                   Location/Qualifiers
misc_feature              1..1125
                          note = Bacillus sp. DSM 8714
source                    1..1125
                          mol_type = unassigned DNA
                          organism = unidentified
SEQUENCE: 1
atgaatcgaa aaccagttaa actaatcgca ggaacagctc ttgttatggg ctttgtcatc   60
agttcatcat ccatatcaac tgccgaggaa acaaaaaaga cttatcttat tggctttgat  120
gctcaggaag aagtcgaaac attcacgaat atggtcgatt ctgagatagg ggctctatct  180
gaagaagaaa ttgatattac ctacgaattt aaagaaatac cggtcgtctc tgctgaaatg  240
agtgaagaag aatatgcagc attactagaa gacccatcga tatcatatat tgaagaagac  300
atcgaagtaa caacaatggc ccaagccatt ccatggggaa ttagtcaaat tagtgcccct  360
gaagcgcaaa ttgctggatt tactggtgag ggtgtaaatg ttgcggtgct ggatactgga  420
atagaggatc accccgattt aaacgttcaa ggcggtgtta gctttgttca aggagagccg  480
gattatcagg atggaaatgg acacggaacc catgtcgccg gtacaatcgc tgcccttgat  540
aacgacgaag gcgtaattgg agtcgcacca aatgcagatc tttatgcagt caaagttctg  600
ggtgcaaatg gttctggctc agtcagctca attgctcaag ggcttgaatg ggcaggagaa  660
aacggaatgg acattgcaaa cttaagctta ggtagctcag cacctagcgc gacactcgag  720
caagcagtgg atgaagcaac cgcaaatggt gtcctcgttg ttgccgcttc tgggaactct  780
ggtgcaagtt ccattggtta tccagctcgc tatgataatg ctatggccgt tggcgccacc  840
gaccagtcag atggcctagc tagcttttct cagtacggtg atggcttaga catcgttgct  900
ccaggtgttg gcatcgatag tacctatcct ggtagctcat acgatagctt aagtggaaca  960
tcaatggcaa caactcatgt tgctggtgcc gcagcattgt tgaaagaaaa gaatccactt 1020
tggtcaaatg aacaaattcg cgctcattta aacgaaactg caactgacct tggcgatatg 1080
tatcgttttg gtaatggact tttaaacgca catgccgctg ttgaa              1125

SEQ ID NO: 2              moltype = AA  length = 375
FEATURE                   Location/Qualifiers
REGION                    1..375
                          note = Bacillus sp. DSM 8714
source                    1..375
                          mol_type = protein
                          organism = unidentified
SEQUENCE: 2
MNRKPVKLIA GTALVMGFVI SSSSISTAEE TKKTYLIGFD AQEEVETFTN MVDSEIGALS   60
EEEIDITYEF KEIPVVSAEM SEEEYAALLE DPSISYIEED IEVTTMAQAI PWGISQISAP  120
EAQIAGFTGE GVNAVAVLDTG IEDHPDLNVQ GGVSFVQGEP DYQDGNGHGT HVAGTIAALD  180
NDEGVIGVAP NADLYAVKVL GANGSGSVSS IAQGLEWAGE NGMDIANLSL GSSAPSATLE  240
QAVDEATANG VLVVAASGNS GASSIGYPAR YDNAMAVGAT DQSDGLASFS QYGDGLDIVA  300
PGVGIDSTYP GSSYDSLSGT SMATPHVAGA AALVKEKNPL WSNEQIRAHL NETATDLGDM  360
YRFGNGLLNA HAAVE                                                   375

SEQ ID NO: 3              moltype = AA  length = 269
FEATURE                   Location/Qualifiers
```

```
REGION                     1..269
                           note = Bacillus sp. DSM 8714
source                     1..269
                           mol_type = protein
                           organism = unidentified
SEQUENCE: 3
AQAIPWGISQ ISAPEAQIAG FTGEGVNVAV LDTGIEDHPD LNVQGGVSFV QGEPDYQDGN    60
GHGTHVAGTI AALDNDEGVI GVAPNADLYA VKVLGANGSG SVSSIAQGLE WAGENGMDIA   120
NLSLGSSAPS ATLEQAVDEA TANGVLVVAA SGNSGASSIG YPARYDNAMA VGATDQSDGL   180
ASFSQYGDGL DIVAPGVGID STYPGSSYDS LSGTSMATPH VAGAAALVKE KNPLWSNEQI   240
RAHLNETATD LGDMYRFGNG LLNAHAAVE                                    269

SEQ ID NO: 4               moltype = DNA  length = 1125
FEATURE                    Location/Qualifiers
misc_feature               1..1125
                           note = Bacillus sp. DSM 8714
source                     1..1125
                           mol_type = unassigned DNA
                           organism = unidentified
SEQUENCE: 4
atgaagaaaa gatcaaacgt tttaatcgca ggaacagcga tcgcaaccat tgctttaata    60
ggaacaccat ccatttcaga agctgcgagg aaaaaaaaat cttatttaat tggctttgat   120
gaacctcaag aagttgagca atttacaaca aatttggaag aagagattcg tacacaagca   180
gatgatgcta ttgatgtaac gtacgagttt aaagatattc ctgttcttgc cgtagatatg   240
acggaagaag aaatgactga actcaaaaat gaagagagta tttcctatat tgaagaagat   300
caagaagtga caacgatggc gcaaaagcat tccatgtggg ttgaaagaat tggcacgcca   360
gcagcacacg catcaggatt cacaggtagc ggtgtaagtg tcgcggtcct tgatacaggg   420
attgatccac attctgactt aaatgtacaa gggggggtta gttttgtacc aggcgaaagt   480
ggagcagatg atggaaatgg cacggtact catgtagcag gaacgattgc agcgttagat   540
aatgatgaag gcgttttagg cgttgctcca gaggttgatc tctttgcagt aaaagtttta   600
agtgcatctg gatcaggatc aattagttcg attgcgcaag gtttagagtg gacagctgaa   660
aacaacattg atgtggctaa tttaagctta ggcagtccct ctcctagtca gacgctagaa   720
caagcggtta atgacgccac agatagtggt gtgcttgtag tagcagcagc agggaattct   780
ggaacaagct cattaggtta tccagctcgt tatgataatg ctatggctgt tggcgctacc   840
gaccaatccg atagcttggc tagcttctca cagtatggcg agggtcttga cttagtcgtt   900
cctggtgttg gtgtagaaag cacgtaccca ggtggaggtt atgacagctt aagcggcaca   960
tctatgctgc tccacatgt tgcaggtgca gcagcactcg ttaaacaaaa aaatccaggc  1020
tggacaaacg aacaaatacg aagccattta aacgatacag ccaatgatct tggcgattcg  1080
ttccgcttcg gtagtggctt attgaatgcc gaaaatgccg ttcaa                 1125

SEQ ID NO: 5               moltype = AA  length = 375
FEATURE                    Location/Qualifiers
REGION                     1..375
                           note = Bacillus sp. DSM 8714
source                     1..375
                           mol_type = protein
                           organism = unidentified
SEQUENCE: 5
MKKRSNVLIA GTAIATIALI GTPSISEAAE EKKSYLIGFD EPQEVEQFTT NLEEEIRTQA    60
DDAIDVTYEF KDIPVLAVDM TEEEMTELKN EESISYIEED QEVTTMAQSI PWGIERIGTP   120
AAHASGFTGS GVSVAVLDTG IDPHSDLNVQ GGVSFVPGES GADDGNGHGT HVAGTIAALD   180
NDEGVLGVAP EVDLFAVKVL SASGSGSISS IAQGLEWTAE NNIDVANLSL GSPSPSQTLE   240
QAVNDATDSG VLVVAAAGNS GTSSLGYPAR YDNAMAVGAT DQSDSLASFS QYEGGLDLVA   300
PGVGVESTYP GGGYDSLSGT SMAAPHVAGA AALVKQKNPG WTNEQIRSHL NDTANDLGDS   360
FRFGSGLLNA ENAVQ                                                   375

SEQ ID NO: 6               moltype = AA  length = 269
FEATURE                    Location/Qualifiers
REGION                     1..269
                           note = Bacillus sp. DSM 8714
source                     1..269
                           mol_type = protein
                           organism = unidentified
SEQUENCE: 6
AQSIPWGIER IGTPAAHASG FTGSGVSVAV LDTGIDPHSD LNVQGGVSFV PGESGADDGN    60
GHGTHVAGTI AALDNDEGVL GVAPEVDLFA VKVLSASGSG SISSIAQGLE WTAENNIDVA   120
NLSLGSPSPS QTLEQAVNDA TDSGVLVVAA AGNSGTSSLG YPARYDNAMA VGATDQSDSL   180
ASFSQYEGGL DLVAPGVGVE STYPGGGYDS LSGTSMAAPH VAGAAALVKQ KNPGWTNEQI   240
RSHLNDTAND LGDSFRFGSG LLNAENAVQ                                    269

SEQ ID NO: 7               moltype = DNA  length = 1149
FEATURE                    Location/Qualifiers
source                     1..1149
                           mol_type = unassigned DNA
                           organism = Bacillus pseudalcaliphilus
                           strain = Bacillus pseudalcaliphilus DSM 8725
SEQUENCE: 7
gtgaatcaag gatggaaaaa acttctcaca atgacagcgg ttgttttatt attttccatta    60
acaagtatga cagtattggc agatgaagag aaaaagacct atttaatcgg gttccataat   120
```

```
cagctagatg tcaacgaatt tattgaggag gatgtaacga atacaaatgg cgtgcaatta    180
tatacgtcag aggataagtc tgcacagsta caattagagg tcttacatga atttgagcaa    240
atcccagttg ttgctgttga gctgagtcca gctgatatca aggcattaga ggcagagtca    300
ggtattgcct atattgaaga agactttgac gttacgattg cgaaccaaac cgtaccgtgg    360
ggaatcgctc aggtacaagc tccacaagcg catgaattag gccacagtgg gtcaggaaca    420
aaagtagcgg tacttgatac tggtattgct gagcatgctg atttattcat tcatggagga    480
gcaagctttg ttgcaggtga gccagattat catgatttaa atgggcacgg aactcacgta    540
gcaggaacaa tcgctgcact taatgatgga gccggagtaa tcggtgttgc accagacgca    600
gaattatatg cggtcaaagt attagggca agtggtagtg gttcggtaag ttcaattgca    660
caaggtttta aatgggctgg tgataatggt atggacgtag ccaatctaag cttaggtagc    720
ccggttggta gtgatacgtt agagcaagca gttaattacg caacggattc aggggttctt    780
gttgtgctc cttctggtaa tagtgggtca gggactgttt cttacccagc tcgatatgat    840
aacgcatttg ctgttggtgc aacagaccaa gtgaataacc gtgcaagctt ttcacaatat    900
ggaacgtgggt tagatattgt cgcacctggt gttgaagttg aaagtacgta cttaaatggt    960
gagtatgcga gcttgagtgg tacttccatg gcgacaccac atgtcgcggg ggtcgcggcg   1020
ttaataaaag ctaaaaatcc aatgttatct aatgaagaga ttcgtcagca attagttcag   1080
acagctacac gttaggaag tgctgatatg tatgaagtg gtttagttaa tgcagaggtg    1140
gctgtacaa                                                            1149

SEQ ID NO: 8           moltype = AA  length = 383
FEATURE                Location/Qualifiers
source                 1..383
                       mol_type = protein
                       note = Bacillus pseudalcaliphilus DSM 8725
                       organism = Bacillus pseudalcaliphilus
SEQUENCE: 8
VNQGWKKLLT MTAVVLLFSL TSMTVLADEE KKTYLIGFHN QLDVNEFIEE DVTNTNGVQL     60
YTSEDKSAQV QLEVLHEFEQ IPVVAVELSP ADIKALEAES GIAYIEEDFD VTIANQTVPW    120
GIAQVQAPQA HELGHSGSGT KVAVLDTGIA EHADLFIHGG ASFVAGEPDY HDLNGHGTHV    180
AGTIAALNDG AGVIGVAPDA ELYAVKVLGA SGSGSVSSIA QGLEWAGDNG MDVANLSLGS    240
PVGSDTLEQA VNYATDSGVL VVAASGNSGS GTVSYPARYD NAFAVGATDQ VNNRASFSQY    300
GTGLDIVAPG VEVESTYLNG EYASLSGTSM ATPHVAGVAA LIKAKNPMLS NEEIRQQLVQ    360
TATPLGSADM YGSGLVNAEV AVQ                                            383

SEQ ID NO: 9           moltype = AA  length = 269
FEATURE                Location/Qualifiers
source                 1..269
                       mol_type = protein
                       note = Bacillus pseudalcaliphilus DSM 8725
                       organism = Bacillus pseudalcaliphilus
SEQUENCE: 9
NQTVPWGIAQ VQAPQAHELG HSGSGTKVAV LDTGIAEHAD LFIHGGASFV AGEPDYHDLN     60
GHGTHVAGTI AALNDGAGVI GVAPDAELYA VKVLGASGSG SVSSIAQGLE WAGDNGMDVA    120
NLSLGSPVGS DTLEQAVNYA TDSGVLVVAA SGNSGSGTVS YPARYDNAFA VGATDQVNNR    180
ASFSQYGTGL DIVAPGVEVE STYLNGEYAS LSGTSMATPH VAGVAALIKA KNPMLSNEEI    240
RQQLVQTATP LGSADMYGSG LVNAEVAVQ                                      269

SEQ ID NO: 10          moltype = DNA  length = 1125
FEATURE                Location/Qualifiers
source                 1..1125
                       mol_type = unassigned DNA
                       organism = Bacillus oshimensis
SEQUENCE: 10
atgaagaaaa gaacacacgt attaattgca ggaacagcag tcgcaaccat tgctttaata     60
ggaacaccat ccatttcaga agcagcagag gaaaaaaaat cttatttaat tggctttgat    120
gaacctcagg aagtggagca atttacaaca aatttagcag aagagattcg cacacaagca    180
gatgatgcga ttgatgtaac gtacgaattt aaggagattc ctgttcttgc agtagaaatg    240
acagaagaag agatggctga actcaaaaat aaggagagta tttcctatat tgaagaggat    300
caagaagtga caacgatggc acaaaagcatt ccatgggaa tcgaaagaat tggcacgcca    360
gctgcacaga cctcaggatt tacaggcagt ggtgtaagtg tagcgtcct tgatacagga    420
attgatccac actctgactt aaatatacaa ggtggcgtta gttttgtacc aggcgaaagt    480
gggtcagatg atggaaatgg acacggtact catgtagcag gtacgattgc agcgttagat    540
aatgatcaag gggtattggg tgttgcgcca gacgttgatc tttttgcagt aaaagtctta    600
agtgcttctg gatcaggatc gattagttcg attgcgcaag gtttagagtg gacagcagaa    660
aacaatattg atgtagccaa tctaagttta ggaagcccct ctcctagtca gacattagag    720
caagcggtta atgatccac agatagcggt gtcttgtag tagcagcagc agggaattct    780
gggacaagtt cattaggata tccagctcgt tatgatcatg caatggctgt tggcgctacc    840
gatgagtcgg atagtctcgc tagcttctca cagtatggag agggactcga tttagtcgga    900
cctggccgttg gtgtagaaag tacgtaccca ggtgaggtt atgacagctt aagcggaaca    960
tctatggctg ctccacatgt tgcaggtgcc gcagcactcg ttaagcaaaa aaatccaagc   1020
tggacaaacg aacaaatacg aggccattta aacgatacag ccaatgatct tggcgattcg   1080
ttccgctttg gtagtggctt actgaatgtt gaaaatgccg ttcaa                   1125

SEQ ID NO: 11          moltype = AA  length = 375
FEATURE                Location/Qualifiers
source                 1..375
                       mol_type = protein
                       organism = Bacillus oshimensis
SEQUENCE: 11
```

```
MKKRTHVLIA GTAVATIALI GTPSISEAAE EKKSYLIGFD EPQEVEQFTT NLAEEIRTQA    60
DDAIDVTYEF KEIPVLAVEM TEEEMAELKN EESISYIEED QEVTTMAQSI PWGIERIGTP   120
AAQASGFTGS GVSVAVLDTG IDPHSDLNIQ GGVSFVPGES GSDDGNGHGT HVAGTIAALD   180
NDQGVLGVAP DVDLFAVKVL SASGSGSISS IAQGLEWTAE NNIDVANLSL GSPSPSQTLE   240
QAVNDATDSG VLVVAAAGNS GTSSLGYPAR YDHAMAVGAT DESDSLASFS QYEGGLDLVA   300
PGVGVESTYP GGGYDSLSGT SMAAPHVAGA AALVKQKNPS WTNEQIRGHL NDTANDLGDS   360
FRFGSGLLNV ENAVQ                                                    375

SEQ ID NO: 12           moltype = AA   length = 269
FEATURE                 Location/Qualifiers
source                  1..269
                        mol_type = protein
                        organism = Bacillus oshimensis
SEQUENCE: 12
AQSIPWGIER IGTPAAQASG FTGSGVSVAV LDTGIDPHSD LNIQGGVSFV PGESGSDDGN    60
GHGTHVAGTI AALDNDQGVL GVAPDVDLFA VKVLSASGSG SISSIAQGLE WTAENNIDVA   120
NLSLGSPSPS QTLEQAVNDA TDSGVLVVAA AGNSGTSSLG YPARYDHAMA VGATDESDSL   180
ASFSQYEGGL DLVAPGVGVE STYPGGGYDS LSGTSMAAPH VAGAAALVKQ KNPSWTNEQI   240
RGHLNDTAND LGDSFRFGSG LLNVENAVQ                                     269

SEQ ID NO: 13           moltype = DNA   length = 1125
FEATURE                 Location/Qualifiers
source                  1..1125
                        mol_type = unassigned DNA
                        organism = Bacillus patagoniensis
SEQUENCE: 13
atgaatcgaa aaccagttaa actaatcgca ggaacagttc ttgttatggg ctttgtcatc    60
agttcatcat ccatatcaac tgccgaggaa acaaaaaaga cttatcttat tggttttgac   120
gctcaggaag aagtcgaaac attcacgaat atcgttgatt ctgagatagg ggctttatct   180
gaagaagata ttgacattac ctacgaattt aaagacataa cggtcgtctc tgctgaaatg   240
agtgatgagg agtatgcagc attactagaa gacccatcga tatcatatat tgaagaagac   300
atcgaagtaa caacaatggc ccaaaccatt ccatggggca ttagtcaaat tagtgctcct   360
gaagcacaaa tcgctggatt tactggtgag gcgtaaacg tcgcggtgct ggatactgga   420
atagaagatc accccgactt aaacgttcaa ggcggtgtta gctttgttca aggagagccg   480
gattatcagg atggaaatgg cacacggaacc catgtcgccg gtacaatcgc tgcccttgat   540
aacgacgaag gcgtaattgg agtcgcacca aatgcagatc tttatgcagt caaagttctt   600
ggtgcaaatg gttcaggctc ggtcagctca attgctcaag gcttgaatg gcaggagaa    660
aatgggatgg acattgcaaa cttaagccta ggtagctctg cacctagcgc gacactcgag   720
caagcagtgg atgaagcaac cgcaaatggc gtcctcgttg tagccgcttc tgggaactcg   780
ggtgcaagtt ctattggtta ccggctcgc tatgataacg ctatggccgt tggcgccacc    840
gaccagtcag acagcctagc taactttctt caatatggcg aaggcttaga cattgtagct   900
ccaggtgttg gcatcgatag tacctatact ggcagctcat acgacagctt aagtggaaca   960
tcaatggcca cccctcatgt tgctggatcc agcagcattg gtgaaagaaaa gaatccactt  1020
tggtcaaatg aacaaattcg tgctcattta aacgaaactg caactgacct tggagatacg  1080
tatcgtttg gtaatgggct tttaaacgca catgccgctg ttgaa                   1125

SEQ ID NO: 14           moltype = AA   length = 375
FEATURE                 Location/Qualifiers
source                  1..375
                        mol_type = protein
                        organism = Bacillus patagoniensis
SEQUENCE: 14
MNRKPVKLIA GTVLVMGFVI SSSSISTAEE TKKTYLIGFD AQEEVETFTN IVDSEIGALS    60
EEDIDITYEF KDIPVVSAEM SDEEYAALLE DPSISYIEED IEVTTMAQTI PWGISQISAP   120
EAQIAGFTGE GVNVAVLDTG IEDHPDLNVQ GGVSFVQGEP DYQDGNGHGT HVAGTIAALD   180
NDEGVIGVAP NADLYAVKVL GANGSGSVSS IAQGLEWAGE NGMDIANLSL GSSAPSATLE   240
QAVDEATANG VLVVAASGNS GASSIGYPAR YDNAMAVGAT DQSDSLANFS QYEGGLDIVA   300
PGVGIDSTYT GSSYDSLSGT SMATPHVAGS AALVKEKNPL WSNEQIRAHL NETATDLGDT   360
YRFGNGLLNA HAAVE                                                    375

SEQ ID NO: 15           moltype = AA   length = 269
FEATURE                 Location/Qualifiers
source                  1..269
                        mol_type = protein
                        organism = Bacillus patagoniensis
SEQUENCE: 15
AQTIPWGISQ ISAPEAQIAG FTGEGVNVAV LDTGIEDHPD LNVQGGVSFV QGEPDYQDGN    60
GHGTHVAGTI AALDNDEGVI GVAPNADLYA VKVLGANGSG SVSSIAQGLE WAGENGMDIA   120
NLSLGSSAPS ATLEQAVDEA TANGVLVVAA SGNSGASSIG YPARYDNAMA VGATDQSDSL   180
ANFSQYEGGL DIVAPGVGID STYTGSSYDS LSGTSMATPH VAGSAALVKE KNPLWSNEQI   240
RAHLNETATD LGDTYRFGNG LLNAHAAVE                                     269

SEQ ID NO: 16           moltype = DNA   length = 1041
FEATURE                 Location/Qualifiers
misc_feature            1..1041
                        note = Synthetic Construct
source                  1..1041
                        mol_type = other DNA
                        organism = synthetic construct
```

```
SEQUENCE: 16
gaggaaacaa aaaagactta tcttattggc tttgatgctc aggaagaagt cgaaacattc    60
acgaatatgg tcgattctga gatagggct ctatctgaag aagaaattga tattacctac    120
gaatttaaag aaataccggt cgtctctgct gaaatgagtg aagaagaata tgcagcatta    180
ctagaagacc catcgatatc atatattgaa gaagacataa agtaacaac aatgcccaa    240
gccattccat ggggaattag tcaaattagt gcccctgaag cgcaaattgc tggatttact   300
ggtgagggtg taaatgttgc ggtgctggat actggaatag aggatcaccc cgatttaaac   360
gttcaaggcg tgttagctt tgttcaagga gagccggatt atcaggatgg aaatggacac   420
ggaacccatg tcgccggtac aatcgctgcc cttgataacg acgaaggcgt aattggagtc   480
gcaccaaatg cagatcttta tgcagtcaaa gttctgggtg caaatggttc tggctcagtc   540
agctcaattg ctcaagggct tgaatgggca ggagaaaacg gaatggacat tgcaaactta   600
tcattaggta gctcagcacc tagcgcgaca ctggaacaag cagtggatga agcaaccgca   660
aatggtgtcc tcgttgttgc cgcttctggg aactctggtg caagttccat tggttatcca   720
gctcgctatg ataatgctat ggccgttggc gccaccgacc agtcagatgg cctagcatca   780
ttttctcagt acggtgatgg cttagacatc gttgctccag tgttggcat cgatagtacc   840
tatcctggta gctcatacga tagcttaagt ggaacatcaa tggcaacacc tcatgttgct   900
ggtgccgcag cattggtgaa agaaaagaat ccactttggt caaatgaaca aattcgcgct   960
catttaaacg aaactgcaac tgaccttggc gatatgtatc gttttggtaa tggacttttta  1020
aacgcacatg ccgctgttga a                                             1041

SEQ ID NO: 17          moltype = AA  length = 347
FEATURE                Location/Qualifiers
REGION                 1..347
                       note = Protein expressed from synthetic construct
source                 1..347
                       mol_type = protein
                       organism = synthetic construct
SEQUENCE: 17
EETKKTYLIG FDAQEEVETF TNMVDSEIGA LSEEEIDITY EFKEIPVVSA EMSEEEYAAL   60
LEDPSISYIE EDIEVTTMAQ AIPWGISQIS APEAQIAGFT GEGVNVAVLD TGIEDHPDLN   120
VQGGVSFVQG EPDYQDGNGH GTHVAGTIAA LDNDEGVIGV APNADLYAVK VLGANGSGSV   180
SSIAQGLEWA GENGMDIANL SLGSSAPSAT LEQAVDEATA NGVLVVAASG NSGASSIGYP   240
ARYDNAMAVG ATDQSDGLAS FSQYGDGLDI VAPGVGIDST YPGSSYDSLS GTSMATPHVA   300
GAAALVKEKN PLWSNEQIRA HLNETATDLG DMYRFGNGLL NAHAAVE                 347

SEQ ID NO: 18          moltype = DNA  length = 1041
FEATURE                Location/Qualifiers
misc_feature           1..1041
                       note = Synthetic Construct
source                 1..1041
                       mol_type = other DNA
                       organism = synthetic construct
SEQUENCE: 18
gcagaggaaa aaaatctta tttaattggc tttgatgaac ctcaagaagt tgagcaattt    60
acaacaaatt tggaagaaga gattcgtaca caagcagatg atgctattga tgtaacgtac   120
gagtttaaag atattcctgt tcttgccgta gatatgacgg aagaagaaat gactgaactc   180
aaaaatgaag agagtatttc ctatattgaa gaagatcaaa gtgacaacag gatggcgcaa   240
agcattccat ggggaattga agaattggc acgccagcag cacacgcatc aggattcaca   300
ggtagcggtg taagtgtcgc ggtccttgat acagggattg atccacattc tgacttaaat   360
gttcaagggg gggttagttt tgtaccaggc gaaagtggag cagatgatgg aaatggacac   420
ggtactcatg tagcaggaac gattgcagcg ttagataatg atgaaggcgt tttaggcgtt   480
gctccagagg ttgatctctt tgcagtaaaa gttttaagtg catctggatc aggatcaatt   540
agttcgattg cgcaaggttt agagtggaca gctgaaaaca acattgatgt ggctaattta   600
tctttaggca gtccctctcc tagtcagacg ctagaacaag cggttaatga cgccacagat   660
agtggtgtgc ttgtagtagc agcagcaggg aactctggaa caagtcatt aggttatcca   720
gctcgttatg ataatgcaat ggctgttggc gctaccgacc aatccgatag cctggcatca   780
ttctcacagt atggcgaggg tcttgactta gtcgctcctg gtgttggtgt agaaagcacg   840
tacccaggtg gaggttatga cagcttaagc ggcacatcta tggctgctcc acatgttgca   900
ggtgcagcag cactcgttaa acaaaaaaat ccaggctgga caaacgaaca atacgaagc   960
catttaaacg atacagccaa tgatcttggc gattcgttcc gcttcggtag tggcttattg  1020
aatgccgaaa atgccgttca a                                             1041

SEQ ID NO: 19          moltype = AA  length = 347
FEATURE                Location/Qualifiers
REGION                 1..347
                       note = Protein expressed from synthetic construct
source                 1..347
                       mol_type = protein
                       organism = synthetic construct
SEQUENCE: 19
AEEKKSYLIG FDEPQEVEQF TTNLEEEIRT QADDAIDVTY EFKDIPVLAV DMTEEEMTEL   60
KNEESISYIE EDQEVTTMAQ SIPWGIERIG TPAAHASGFT GSGVSVAVLD TGIDPHSDLN   120
VQGGVSFVPG ESGADDGNGH GTHVAGTIAA LDNDEGVLGV APEVDLFAVK VLSASGSGSI   180
SSIAQGLEWT AENNIDVANL SLGSPSPSQT LEQAVNDATD SGVLVVAAAG NSGTSSLGYP   240
ARYDNAMAVG ATDQSDSLAS FSQYGEGLDL VAPGVGVEST YPGGGYDSLS GTSMAAPHVA   300
GAAALVKQKN PGWTNEQIRS HLNDTANDLG DSFRFGSGLL NAENAVQ                 347

SEQ ID NO: 20          moltype = DNA  length = 1068
FEATURE                Location/Qualifiers
```

```
misc_feature            1..1068
                        note = Synthetic Construct
source                  1..1068
                        mol_type = other DNA
                        organism = synthetic construct
SEQUENCE: 20
gatgaagaga aaaagaccta tttaatcggg ttccataatc agctagatgt caacgaattt    60
attgaggagg atgtaacgaa tacaaatggc gtgcaattat atacgtcaga ggataagtct   120
gcacaggtac aattagaggt cttacatgaa tttgagcaaa tcccagttgt tgctgttgag   180
ctgagtccag ctgatatcaa ggcattagag gcagagtcag gtattgccta tattgaagaa   240
gactttgacg ttacgattgc gaaccaaacc gtaccgtggg gaatcgctca ggtacaagct   300
ccacaagcgc atgaattagg ccacagtggg tcaggaacaa aagtagcggt acttgatact   360
ggtattgctg agcatgctga tttattcatt catggaggag catcatttgt tgcaggtgag   420
ccagattatc atgatttaaa tgggcacgga actcacgtag caggaacaat cgctgcactt   480
aatgatggag ccggagtaat cggtgttgca ccagacgcga aattatatgc ggtcaaagta   540
ttaggggcaa gtggtagtgg ttcggtaagt tcaattgcac aaggtttaga atgggctggt   600
gataatggta tggacgtagc caatctatca ttaggtagcc cggttggtag tgatacgtta   660
gagcaagcag ttaattacgc aacggattca ggggttcttg ttgtggctgc ttctggtaat   720
agtgggtcag ggactgtttc ttacccagct cgatatgata acgcatttgc tgttggtgca   780
acagaccaag tgaataaccg tgcatcattt tcacaatatg gaacggggtt agatattgtc   840
gcacctggtg ttgaagttga aagtacgtac ttaaatggtg agtatgcgag cttgagtggt   900
acttccatgg cgacaccaca tgtcgcgggg gtcgcgcctt aataaaagc taaaaatcca   960
atgttatcta atgaagagat tcgtcagcaa ttagttcaga cagctacacc gttaggaagt  1020
gctgatatgt atggaagtgg tttagttaat gcagaggtgg ctgttcaa                1068

SEQ ID NO: 21           moltype = AA   length = 356
FEATURE                 Location/Qualifiers
REGION                  1..356
                        note = Protein expressed from synthetic construct
source                  1..356
                        mol_type = protein
                        organism = synthetic construct
SEQUENCE: 21
DEEKKTYLIG FHNQLDVNEF IEEDVTNTNG VQLYTSEDKS AQVQLEVLHE FEQIPVVAVE    60
LSPADIKALE AESGIAYIEE DFDVTIANQT VPWGIAQVQA PQAHELGHSG SGTKVAVLDT   120
GIAEHADLFI HGGASFVAGE PDYHDLNGHG THVAGTIAAL NDGAGVIGVA PDAELYAVKV   180
LGASGSGSVS SIAQGLEWAG DNGMDVANLS LGSPVGSDTL EQAVNYATDS GVLVVAASGN   240
SGSGTVSYPA RYDNAFAVGA TDQVNNRASF SQYGTGLDIV APGVEVESTY LNGEYASLSG   300
TSMATPHVAG VAALIKAKNP MLSNEEIRQQ LVQTATPLGS ADMYGSGLVN AEVAVQ       356

SEQ ID NO: 22           moltype = DNA   length = 1041
FEATURE                 Location/Qualifiers
misc_feature            1..1041
                        note = Synthetic Construct
source                  1..1041
                        mol_type = other DNA
                        organism = synthetic construct
SEQUENCE: 22
gcagaggaaa aaaatctta tttaattggc tttgatgaac ctcaggaagt ggagcaattt     60
acaacaaatt tagcagaaga gattcgcaca caagcagatg atgcgattga tgtaacgtac   120
gaatttaagg agattcctgt tcttgcagta gaaatgacaa aagaagagat cgctgaactc   180
aaaaatgaag agagtatttc ctatattgaa gaggatcaag aagtgacaac gatggcacaa   240
agcattccat ggggaatcga aagaattggc acgccagctg cacaggcctc aggatttaca   300
ggcagtggtg taagtgtagc agtccttgat acaggaattg atccacactc tgacttaaat   360
atacaaggtg gcgttagttt tgtaccaggc gaaagtgatg acggatgtga aatggacac    420
ggtactcatg tagcaggtac gattgcagcg ttagataatg atcaagggt attgggtgtt   480
gcgccagacg ttgatctttt tgcagtaaaa gtcttaagtg cttctggatc aggatcgatt   540
agttcgattg cgcaagggtt agagtggaca gcagaaaaca atattgatgt agccaatcta   600
agtttaggaa gccccctctcc tagtcagaca ttagagcaag cggttaatga tgccacagat   660
agcggtgtgc ttgtagtagc agcagcaggg aactctggga caagttcatt aggatatcca   720
gctcgttatg atcatgcaat ggctgttggc gctaccgatg agtcggatag tctcgcatca   780
ttctcacagt atggagaggg actcgattta gtcgcacctg gcgttggtgt agaaagtacg   840
tacccaggtg gaggttatga cagcttaagc ggaacatcta tggctgctcc acatgttgca   900
ggtgccgcag cactcgttaa gcaaaaaaat ccaagctgca caaacgaaca aatacgaggc   960
catttaaacg atacagccaa tgatcttggc gattcgtcc gctttggtag tggcttactg  1020
aatgttgaaa atgccgttca a                                              1041

SEQ ID NO: 23           moltype = AA   length = 347
FEATURE                 Location/Qualifiers
REGION                  1..347
                        note = Protein expressed from synthetic construct
source                  1..347
                        mol_type = protein
                        organism = synthetic construct
SEQUENCE: 23
AEEKKSYLIG FDEPQEVEQF TTNLAEEIRT QADDAIDVTY EFKEIPVLAV EMTEEEMAEL    60
KNEESISYIE EDQEVTTMAQ SIPWGIERIG TPAAQASGFT GSGVSAVLD TGIDPHSDLN    120
IQGGVSFVPG ESGSDDGNGH GTHVAGTIAA LDNDQGVLGV APDVDLFAVK VLSASGSGSI   180
SSIAQGLEWT AENNIDVANL SLGSPSPSQT LEQAVNDATD SGVLVVAAAG NSGTSSLGYP   240
```

```
ARYDHAMAVG ATDESDSLAS FSQYGEGLDL VAPGVGVEST YPGGGYDSLS GTSMAAPHVA    300
GAAALVKQKN PSWTNEQIRG HLNDTANDLG DSFRFGSGLL NVENAVQ                 347

SEQ ID NO: 24           moltype = DNA   length = 1044
FEATURE                 Location/Qualifiers
misc_feature            1..1044
                        note = Synthetic Construct
source                  1..1044
                        mol_type = other DNA
                        organism = synthetic construct
SEQUENCE: 24
gaggaaacaa aaaagactta tcttattggt tttgacgctc aggaagaagt cgaaacattc    60
acgaatatcg ttgattctga datagggggct ttatctgaag aagatattga cattacctac  120
gaatttaaag acataccggt cgtctctgct gaaatgagtg atgaggaagta tgcagcatta  180
ctagaagacc catcgatatc atataattgaa gaagacatcg aagtaacaac aatgcccaa   240
accattccat ggggcattag tcaaattagt gctcctgaag cacaaatcgc tggatttact   300
ggtgagggcg taaacgtcgc ggtgctggat actggaataa aagatcaccc cgacttaaac   360
gttcaaggcg gtgttagctt tgttcaagga gagccgatt atcaggatga aaatggacac    420
ggaacccatg tcgccggtac aatcgctgcc cttgataacg acgaaggcgt aattggagtc    480
gcaccaaatg cagatcttta tgcagtcaaa gttcttggtg caaatggttc aggctcggtc    540
agctcaattg ctcaagggct tgaatgggca ggagaaaatg gatgggacat tgcaaactta    600
agcctaggta gctctgcacc tagcgcgaca ctggaacaag cagcagatga agcaaccgca    660
aatggcgtcc tcgttgtagc cgcttctggg aactcgggtg caagttctat tggttatccg    720
gctcgctatg ataacgctat ggccgttggc gccaccgacc agtcagacag cctagctaac    780
ttttctcaat atggcgaagg cttagacatt gtagctccag tgttggcat cgatagtacc     840
tatactgcca gctcatacga cagcttaagt ggaacatcaa tggccaccc tcatgttgtt    900
ggctcagcag cattggtgaa agaaaagaat ccactttggt caaatgaaca aattcgtgct    960
catttaaacg aaactgcaac tgaccttgga gatacgtatc gttttggtaa tgggctttta  1020
aacgcacatg ccgctgttga ataa                                         1044

SEQ ID NO: 25           moltype = AA   length = 333
FEATURE                 Location/Qualifiers
REGION                  1..333
                        note = Protein expressed from synthetic construct
source                  1..333
                        mol_type = protein
                        organism = synthetic construct
SEQUENCE: 25
EETKKTYLIG FDAQEEVETF TNIVDSEIGA LSEEDIDITY EFKDIPVVSA EMSDEEYAAL    60
LEDPSISYIE EDIEVTTMAQ TIPWGISQIS APEAQIAGFT GEGVNVAVLD TGIEDHPDLN   120
VQGGVSFVQG EPDYQDGNGH GTHVAGTIAA LDNDEGVIGV APNADLYAVK VLGANGSGSV   180
SSIAQGLEWA GENGMDIANL SLGSSAPSAT LEQAVDEATA NGVLVVAASG NSGASSIGYP   240
ARYDNAMAVG ATDQSDSLAN FSQYGEGLDI VAPGVGIDST YTGSSYDSLS GTSMATPHVA   300
GSAALVKEKN PLWSNEQIRA HLNETATDLG DTY                                333

SEQ ID NO: 26           moltype = AA   length = 20
FEATURE                 Location/Qualifiers
REGION                  1..20
                        note = Protein expressed from synthetic construct
REGION                  5..6
                        note = MISC_FEATURE - X is any amino acid
SITE                    10
                        note = MISC_FEATURE - X is N or S or X is N or X is S
REGION                  14..17
                        note = MISC_FEATURE - X is any amino acid
SITE                    20
                        note = MISC_FEATURE - X is any amino acid
source                  1..20
                        mol_type = protein
                        organism = unidentified
SEQUENCE: 26
DLGDXXRFGX GLLXXXXAVX                                                20

SEQ ID NO: 27           moltype = AA   length = 269
FEATURE                 Location/Qualifiers
REGION                  1..269
                        note = Bacillus sp. DSM 8714
source                  1..269
                        mol_type = protein
                        organism = unidentified
SEQUENCE: 27
AQAIPWGISQ ISAPEAQIAG FTGEGVNVAV LDTGIEDHPD LNVQGGVSFV QGEPDYQDGN    60
GHGTHVAGTI AALDNDEGVI GVAPNADLYA VKVLGANGSG SVSSIAQGLE WAGENGMDIA   120
NLSLGSSAPS ATLEQAVDEA TANGVLVVAA SGNSGASSIG YPARYDNAMA VGATDQSDGL   180
ASFSQYGDGL DIVAPGVGID STYPGSSYDS LSGTSMATPH VAGAAALVKE KNPLWSNEQI   240
RAHLNETATD LGDMYRFGNG LLNAHAAVE                                     269

SEQ ID NO: 28           moltype = AA   length = 269
FEATURE                 Location/Qualifiers
```

| | | |
|---|---|---|
| source | 1..269 | |
| | mol_type = protein | |
| | organism = Bacillus patagoniensis | |
| SEQUENCE: 28 | | |
| AQTIPWGISQ ISAPEAQIAG FTGEGVNVAV LDTGIEDHPD LNVQGGVSFV QGEPDYQDGN | | 60 |
| GHGTHVAGTI AALDNDEGVI GVAPNADLYA VKVLGANGSG SVSSIAQGLE WAGENGMDIA | | 120 |
| NLSLGSSAPS ATLEQAVDEA TANGVLVVAA SGNSGASSIG YPARYDNAMA VGATDQSDSL | | 180 |
| ANFSQYGEGL DIVAPGVGID STYTGSSYDS LSGTSMATPH VAGSAALVKE KNPLWSNEQI | | 240 |
| RAHLNETATD LGDTYRFGNG LLNAHAAVE | | 269 |
| | | |
| SEQ ID NO: 29 | moltype = AA length = 269 | |
| FEATURE | Location/Qualifiers | |
| REGION | 1..269 | |
| | note = Bacillus sp. DSM 8717 | |
| source | 1..269 | |
| | mol_type = protein | |
| | organism = unidentified | |
| SEQUENCE: 29 | | |
| AQSIPWGIER IGTPAAHASG FTGSGVSVAV LDTGIDPHSD LNVQGGVSFV PGESGADDGN | | 60 |
| GHGTHVAGTI AALDNDEGVL GVAPEVDLFA VKVLSASGSG SISSIAQGLE WTAENNIDVA | | 120 |
| NLSLGSPSPS QTLEQAVNDA TDSGVLVVAA AGNSGTSSLG YPARYDNAMA VGATDQSDSL | | 180 |
| ASFSQYGEGL DLVAPGVGVE STYPGGGYDS LSGTSMAAPH VAGAAALVKQ KNPGWTNEQI | | 240 |
| RSHLNDTAND LGDSFRFGSG LLNAENAVQ | | 269 |
| | | |
| SEQ ID NO: 30 | moltype = AA length = 269 | |
| FEATURE | Location/Qualifiers | |
| source | 1..269 | |
| | mol_type = protein | |
| | organism = Bacillus oshimensis | |
| SEQUENCE: 30 | | |
| AQSIPWGIER IGTPAAQASG FTGSGVSVAV LDTGIDPHSD LNIQGGVSFV PGESGSDDGN | | 60 |
| GHGTHVAGTI AALDNDQGVL GVAPDVDLFA VKVLSASGSG SISSIAQGLE WTAENNIDVA | | 120 |
| NLSLGSPSPS QTLEQAVNDA TDSGVLVVAA AGNSGTSSLG YPARYDHAMA VGATDESDSL | | 180 |
| ASFSQYGEGL DLVAPGVGVE STYPGGGYDS LSGTSMAAPH VAGAAALVKQ KNPSWTNEQI | | 240 |
| RGHLNDTAND LGDSFRFGSG LLNVENAVQ | | 269 |
| | | |
| SEQ ID NO: 31 | moltype = AA length = 269 | |
| FEATURE | Location/Qualifiers | |
| REGION | 1..269 | |
| | note = Bacillus sp. B001 | |
| source | 1..269 | |
| | mol_type = protein | |
| | organism = unidentified | |
| SEQUENCE: 31 | | |
| AQSIPWGIER IGTPAAQASG FTGSGVSVAV LDTGIDPHSD LNVQGGVSFV PGESGADDGN | | 60 |
| GHGTHVAGTI AALDNDEGVL GVAPEVDLFA VKVLSASGSG SISSIAQGLE WAAENNIDVA | | 120 |
| NLSLGSPSPS QTLEQAVNDA TDSGVLVVAA AGNSGTSSLG YPARYDNAMA VGATDQSDSL | | 180 |
| ASFSQYGEGL DLVAPGVGVE STYPGGGYDS LSGTSMAAPH VAGAAALVKQ KNPGWTNEQI | | 240 |
| RSHLNDTAND LGDSFRFGSG LLNAENAVQ | | 269 |
| | | |
| SEQ ID NO: 32 | moltype = AA length = 269 | |
| FEATURE | Location/Qualifiers | |
| REGION | 1..269 | |
| | note = Geomicrobium sp. JCM 19038 | |
| source | 1..269 | |
| | mol_type = protein | |
| | organism = unidentified | |
| SEQUENCE: 32 | | |
| SQTIPWGIDR VNAPAANASG VTGGGVSVAI LDTGISTHED LNIQGGESFV PGEPGIDDGN | | 60 |
| GHGTHVAGTI AALDNDLGVL GVSPDVDLYA VKVLGSDGSG NISSIAEGLE WAGENGMDVA | | 120 |
| NMSLGSPLPS PTLEQAVDEA TDRGVLVVAA SGNSGASSIG YPAAYDNAMA VGATTQNDTR | | 180 |
| ASFSQYGAGL DIVAPGVGVE STYPGGGYRS LDGTSMAAPH VAGVAALVLE QNPSWSPQQV | | 240 |
| RNHLNDTATD LGDSNQYGSG LVDAVSATE | | 269 |
| | | |
| SEQ ID NO: 33 | moltype = AA length = 269 | |
| FEATURE | Location/Qualifiers | |
| REGION | 1..269 | |
| | note = Geomicrobium sp. JCM 19055 | |
| source | 1..269 | |
| | mol_type = protein | |
| | organism = unidentified | |
| SEQUENCE: 33 | | |
| SQTVPWGIDR VNAPAANASG VTGGGVSVAV LDTGISTHED LNIQGGESFV PGEPGIDDGN | | 60 |
| GHGTHVAGTI AALDNDTGVV GVSPDADLYA VKVLGSDGSG NISSIAQGLQ WAGENGMDVA | | 120 |
| NMSLGSPLPS PTLEQAVDEA TDRGVLVVAA SGNSGASSLS YPAAYDNAMA VGATTQSDAR | | 180 |
| ASFSQYGAGL DLVAPGVGVE STYPGGGYRS LDGTSMATPH VAGVAALVLE QNPSWSPQQV | | 240 |
| RSHVNDTATD LGDTNQFGSG LVDAESATD | | 269 |
| | | |
| SEQ ID NO: 34 | moltype = AA length = 269 | |

| FEATURE | Location/Qualifiers |
|---|---|
| REGION | 1..269 |
| | note = Geomicrobium sp. JCM 19037 |
| source | 1..269 |
| | mol_type = protein |
| | organism = unidentified |

SEQUENCE: 34
```
SQTIPWGIDR VQATAAHNRG ITGNGVRVAV LDTGISNHPD LNIQGGTSFV PGEPGIADGN    60
GHGTHVAGTI AALDNNVGVL GVAPDVDLFA VKVLGRSGSG SISGIAQGLQ WSSNNNMDVA   120
NMSLGSPSPS PTLERAVNQA TNSGVLVVAA SGNSGASSIG YPARYQNAMA VGATDQNNNR   180
ASFSQFGTGL DIMAPGVGVQ STYPGNGYRS LSGTSMAAPH VAGVAALVMS NNPSWSPAQV   240
RSHLNQTATP IGASNQYGNG LVNANAATQ                                     269
```

| SEQ ID NO: 35 | moltype = AA length = 269 |
|---|---|
| FEATURE | Location/Qualifiers |
| source | 1..269 |
| | mol_type = protein |
| | organism = Bacillus okhensis |

SEQUENCE: 35
```
NQTIPWGITR VQAPAAINRG FTGAGVRVAV LDTGISNHPD LNIRGGVSFV PGESTYQDGN    60
GHGTHVAGTI AALNNSIGVV GVAPNTELYA VKVLGANGSG SISSIAQGLQ WTAQNNIHVA   120
NLSLGSPTGS QTLELAVNQA TSAGVLVVAA SGNNGSGTIS YPARYANALA VGATDQNNNR   180
ASFSQYGTGL NIVAPGVGVQ STYPGNRYAS LSGTSMATPH VAGVAALVKQ KNPGWSNTQI   240
RQHLLNTATP LGSSNQYGSG LVNAEAATR                                     269
```

| SEQ ID NO: 36 | moltype = AA length = 269 |
|---|---|
| FEATURE | Location/Qualifiers |
| source | 1..269 |
| | mol_type = protein |
| | organism = Bacillus gibsonii |

SEQUENCE: 36
```
QQTVPWGITR VQAPAVHNRG ITGSGVRVAI LDSGISAHSD LNIRGGASFV PGEPTTADLN    60
GHGTHVAGTV AALNNSIGVI GVAPNAELYA VKVLGANGSG SVSGIAQGLE WAATNNMHIA   120
NMSLGSDFPS STLERAVNYA TSRDVLVIAA TGNNGSGSVG YPARYANAMA VGATDQNNRR   180
ANFSQYGTGI DIVAPGVNVQ STYPGNRYVS MNGTSMATPH VAGAAALVKQ RYPSWNATQI   240
RNHLKNTATN LGNSSQFGSG LVNAEAATR                                     269
```

| SEQ ID NO: 37 | moltype = AA length = 269 |
|---|---|
| FEATURE | Location/Qualifiers |
| source | 1..269 |
| | mol_type = protein |
| | organism = Bacillus lentus |

SEQUENCE: 37
```
AQSVPWGISR VQAPAAHNRG LTGSGVKVAV LDTGISTHPD LNIRGGASFV PGEPSTQDGN    60
GHGTHVAGTI AALNNSIGVL GVAPSAELYA VKVLGASGSG SVSSIAQGLE WAGNNGMHVA   120
NLSLGSPSPS ATLEQAVNSA TSRGVLVVAA SGNSGAGSIS YPARYANAMA VGATDQNNNR   180
ASFSQYGAGL DIVAPGVNVQ STYPGSTYAS LNGTSMATPH VAGAAALVKQ KNPSWSNVQI   240
RNHLKNTATS LGSTNLYGSG LVNAEAATR                                     269
```

| SEQ ID NO: 38 | moltype = AA length = 269 |
|---|---|
| FEATURE | Location/Qualifiers |
| REGION | 1..269 |
| | note = Bacillus lentus DSM 5483 |
| source | 1..269 |
| | mol_type = protein |
| | organism = unidentified |

SEQUENCE: 38
```
AQSIPWGISR VQAPAAHNRG LTGSGVKVAV LDTGISTHED LNIRGGASFV PGEPSTQDGN    60
GHGTHVAGTI AALNDSIGVL GVAPSAELYA VKVLGADGEG AISSIAQGLE WAGNNGMHVA   120
NLSLGSPSPS ATLEQAVNSA TSRGVLVVAA SGNSGASSIG YPARYANAMA VGATDQNNNR   180
ASFSRYGAGL DIVAPGVNVQ STYPGSTYAS LNGTSMATPH VAGAAALVKQ KNPSWSNVQI   240
RNHLKNTATS LGDTNLYGSG LVNAEAATR                                     269
```

| SEQ ID NO: 39 | moltype = AA length = 269 |
|---|---|
| FEATURE | Location/Qualifiers |
| source | 1..269 |
| | mol_type = protein |
| | organism = Bacillus pseudalcaliphilus |

SEQUENCE: 39
```
NQTVPWGIAQ VQAPQAHELG HSGSGTKVAV LDTGIAEHAD LFIHGGASFV AGEPDYHDLN    60
GHGTHVAGTI AALNDGAGVI GVAPDAELYA VKVLGASGSG SVSSIAQGLE WAGDNGMDVA   120
NLSLGSPVGS DTLEQAVNYA TDSGVLVVAA SGNSGSGTVS YPARYDNAFA VGATDQVNNR   180
ASFSQYGTGL DIVAPGVEVE STYLNGEYAS LSGTSMATPH VAGVAALIKA KNPMLSNEEI   240
RQQLVQTATP LGSADMYGSG LVNAEVAVQ                                     269
```

| SEQ ID NO: 40 | moltype = AA length = 273 |
|---|---|
| FEATURE | Location/Qualifiers |
| source | 1..273 |
| | mol_type = protein |

```
                        organism = Bacillus pseudofirmus
SEQUENCE: 40
AQTVPWGIPY IYSDVVHRQG YFGNGVKVAV LDTGVAPHPD LHIRGGVSFI STENTYVDYN    60
GHGTHVAGTV AALNNSYGVL GVAPGAELYA VKVLDRNGSG SHASIAQGIE WAMNNGMDIA   120
NMSLGSPSGS TTLQLAADRA RNAGVLLIGA AGNSGQQGSS NNMGYPARYA SVMAVGAVDQ   180
NGNRANFSSY GSELEIMAPG VNINSTYLNN GYRSLNGTSM ASPHVAGVAA LVKQKHPHLT   240
AAQIRNRMNQ TAIPLGNSTY YGNGLVDAEY AAQ                                273

SEQ ID NO: 41           moltype = AA   length = 274
FEATURE                 Location/Qualifiers
source                  1..274
                        mol_type = protein
                        organism = Bacillus licheniformis
SEQUENCE: 41
AQTVPYGIPL IKADKVQAQG FKGANVKVAV LDTGIQASHP DLNVGGASF VAGEAYNTDG     60
NGHGTHVAGT VAALDNTTGV LGVAPSVSLY AVKVLNSSGS GSYSGIVSGI EWATTNGMDV   120
INMSLGGASG STAMKQAVDN AYARGVVVVA AAGNSGSSGN TNTIGYPAKY DSVIAVGAVD   180
SNSNRASFSS VGAELEVMAP GAGVYSTYPT NTYATLNGTS MASPHVAGAA ALILSKHPNL   240
SASQVRNRLS STATYLGSSF YYGKGLINVE AAAQ                               274

SEQ ID NO: 42           moltype = AA   length = 276
FEATURE                 Location/Qualifiers
REGION                  1..276
                        note = Bacillus sp. Strain LG12
source                  1..276
                        mol_type = protein
                        organism = unidentified
SEQUENCE: 42
AQTVPYGVPH IKADVAHAQN VTGSGVKVAV LDTGIDASHE DLRVVGGASF VSEEPDALTD    60
GNGHGTHVAG TIAALNNNVG VLGVSYDVDL YAVKVLSAGG SGTLAGIAQG IEWAIDNNMD   120
VINMSLGGST GSTTLKQASD NAYNSGIVVI AAAGNSGSVL GLVNTIGYPA RYDSVIAVGA   180
VDSNNNRASF SSVGSQLEVM APGVAINSTL PGNQYGELNG TSMASPHVAG AAALLLAQNP   240
NLTNVQVRER LRDTATNLGS AFNYGHGVIN LERALQ                             276

SEQ ID NO: 43           moltype = AA   length = 275
FEATURE                 Location/Qualifiers
REGION                  1..275
                        note = Bacillus sp. KSM-LD1
source                  1..275
                        mol_type = protein
                        organism = unidentified
SEQUENCE: 43
AQTTPWGVTH INAHRAHSSG VTGSGVKVAI LDTGIHASHP DLNVRGGASF ISGESNPYID    60
SNGHGTHVAG TVAALNNTVG VLGVAYNAEL YAVKVLSASG SGTLSGIAQG VEWSIANKMD   120
VINMSLGGSS GSTALQRAVD NAYRNNIVVV AAAGNSGAQG NRNTIGYPAR YSSVIAVGAV   180
DSNNNRASFS SVGSELEVMA PGVSILSTVP GSSYASYNGT SMASPHVAGA AALLKAKYPN   240
WSAAQIRNKL NSTTTYLGSS FYYGNGVINV ERALQ                              275

SEQ ID NO: 44           moltype = AA   length = 275
FEATURE                 Location/Qualifiers
REGION                  1..275
                        note = Bacillus sp. Strain LG12
source                  1..275
                        mol_type = protein
                        organism = unidentified
SEQUENCE: 44
AQTVPWGIPH IKADKAHAAG VTGSGVKVAI LDTGIDANHA DLNVKGGASF VSGEPNALQD    60
GNGHGTHVAG TVAALNNTTG VLGVAYNADL YAVKVLSASG SGTLSGIAQG IEWSISNGMN   120
VINMSLGGSS GSTALQQACN NAYNRGIVVI AAAGNSGSSG NRNTMGYPAR YSSVIAVGAV   180
SSNNTRASFS SVGSELEVMA PGVNILSTTP GNNYASFNGT SMAAPHVAGA AALIKAKYPS   240
MTNVQIRERL KNTATNLGDP FFYGKGVINV ESALQ                              275

SEQ ID NO: 45           moltype = AA   length = 275
FEATURE                 Location/Qualifiers
source                  1..275
                        mol_type = protein
                        organism = Bacillus amyloliquefaciens
SEQUENCE: 45
AQSVPYGVSQ IKAPALHSQG YTGSNVKVAV IDSGIDSSHP DLKVAGGASM VPSETNPFQD    60
NNSHGTHVAG TVAALNNSIG VLGVAPSASL YAVKVLGADG SGQYSWIING IEWAIANNMD   120
VINMSLGGPS GSAALKAAVD KAVASGVVVV AAAGNEGTSG SSSTVGYPGK YPSVIAVGAV   180
DSSNQRASFS SVGPELDVMA PGVSIQSTLP GNKYGAYNGT SMASPHVAGA AALILSKHPN   240
WTNTQVRSSL ENTTTKLGDS FYYGKGLINV QAAAQ                              275

SEQ ID NO: 46           moltype = AA   length = 275
FEATURE                 Location/Qualifiers
source                  1..275
                        mol_type = protein
                        organism = Bacillus atrophaeus
```

```
SEQUENCE: 46
AQSVPYGISQ IKAPAVHSQG YTGSNVKVAV IDSGIDSSHP DLKVSGGASF VPSEPNPFQD   60
GNSHGTHVAG TVAALNNSVG VLGVAPSASL YAVKVLSSSG SGDYSWIING IEWAISNNMD  120
VINMSLGGPQ GSTALKAVVD KAVSQGIVVV AAAGNSGSSG STSTVGYPAK YPSVIAVGAV  180
DSNNQRASFS SAGSELDVMA PGVSIQSTLP GSSYGSYNGT SMASPHVAGA AALVLSKHPN  240
WTNSQVRNSL ESTATNLGNS FYYGKGLINV QAAAQ                            275
```